United States Patent
Tsao et al.

(10) Patent No.: US 10,436,778 B2
(45) Date of Patent: Oct. 8, 2019

(54) METHODS AND SYSTEMS FOR MULTIPLEX ASSAYS

(71) Applicant: PLEXBIO CO., LTD., Taipei (TW)

(72) Inventors: Dean Tsao, Hillsborough, CA (US); Chin-Shiou Huang, Belmont, CA (US)

(73) Assignee: PLEXBIO CO., LTD., Taipei (TW)

( * ) Notice: Subject to any disclaimer, the term of this patent is extended or adjusted under 35 U.S.C. 154(b) by 562 days.

(21) Appl. No.: 14/208,481

(22) Filed: Mar. 13, 2014

(65) Prior Publication Data

US 2014/0274778 A1    Sep. 18, 2014

Related U.S. Application Data

(60) Provisional application No. 61/791,684, filed on Mar. 15, 2013.

(51) Int. Cl.
| | |
|---|---|
| *G01N 33/543* | (2006.01) |
| *C40B 30/04* | (2006.01) |
| *C40B 40/04* | (2006.01) |
| *C40B 50/16* | (2006.01) |

(52) U.S. Cl.
CPC ....... *G01N 33/54313* (2013.01); *C40B 30/04* (2013.01); *C40B 40/04* (2013.01); *C40B 50/16* (2013.01)

(58) Field of Classification Search
CPC .............................................. G01N 33/54313
See application file for complete search history.

(56) References Cited

U.S. PATENT DOCUMENTS

| | | | |
|---|---|---|---|
| 4,677,045 A | 6/1987 | Champ et al. | |
| 5,237,498 A | 8/1993 | Tenma et al. | |
| 5,354,873 A | 10/1994 | Allen et al. | |
| 5,492,795 A | 2/1996 | Allen et al. | |
| 5,641,634 A * | 6/1997 | Mandecki | C12Q 1/6825 340/10.3 |
| 5,656,750 A | 8/1997 | Allen et al. | |
| 5,795,981 A | 8/1998 | Lee et al. | |
| 6,916,661 B2 * | 7/2005 | Chandler | C12Q 1/6816 435/7.1 |
| 7,884,719 B2 | 2/2011 | Oberle | |
| 10,019,815 B2 | 7/2018 | Chung et al. | |
| 2002/0094116 A1 | 7/2002 | Frost et al. | |
| 2002/0150909 A1 * | 10/2002 | Stuelpnagel | B01J 19/0046 435/6.1 |
| 2002/0155618 A1 * | 10/2002 | O'Hagan | G01N 15/1459 436/172 |
| 2003/0134330 A1 | 7/2003 | Ravkin et al. | |

(Continued)

FOREIGN PATENT DOCUMENTS

WO    1997/015390 A1    5/1997

OTHER PUBLICATIONS

Sukhanova et al. (Nano Letters, 2007, 7(8):2322-2327) (Year: 2007).*

(Continued)

*Primary Examiner* — Jeremy C Flinders
(74) *Attorney, Agent, or Firm* — Morrison and Foerster LLP

(57) ABSTRACT

Disclosed herein are compositions comprising beads with unique identifiers for storing information about a multiplex assay as well as methods for using the same in multiplex chemical and biological assays.

32 Claims, 3 Drawing Sheets

(56) References Cited

U.S. PATENT DOCUMENTS

| | | | |
|---|---|---|---|
| 2006/0205115 A1 | 9/2006 | Oberle | |
| 2007/0238140 A1 | 10/2007 | Pentoney et al. | |
| 2008/0129455 A1 | 6/2008 | Oberle | |
| 2009/0032592 A1 | 2/2009 | Christensen | |
| 2010/0246005 A1* | 9/2010 | Moon | B01L 3/54 359/569 |
| 2010/0248257 A1* | 9/2010 | Jacobsen | B82Y 5/00 435/7.1 |
| 2011/0007955 A1 | 1/2011 | Ho et al. | |
| 2017/0146545 A1 | 5/2017 | Chung et al. | |
| 2017/0160272 A1 | 6/2017 | Tsao et al. | |
| 2017/0270690 A1 | 9/2017 | Chung et al. | |
| 2018/0195113 A1 | 7/2018 | Tsao et al. | |
| 2018/0201983 A1 | 7/2018 | Tsao et al. | |

OTHER PUBLICATIONS

Zhang et al. (J. Amer. Chem. Soc., 2007, 129:8424-8425) (Year: 2007).*

International Search Report received for PCT Patent Application No. PCT/US2014/028246, dated Aug. 11, 2014, 4 pages.

Law et al., "Squaraine Chemistry. Synthesis, Characterization, and Optical Properties of a Class of Novel Unsymmetrical Squaraines: [4-(Dimethylamino)phenyl](4'-Methoxyphenyl)Squaraine and its Derivatives", The Journal of Organic Chemistry, vol. 57, No. 12, 1992, pp. 3278-3286.

Maahs et al., "Syntheses and Derivatives of Squaric Acid", Angewandte Chemie International Edition, vol. 5, No. 10, 1966, pp. 888-893.

Needels et al., "Generation and Screening of an Oligonucleotide-Encoded Synthetic Peptide Library", Proc. Natl. Acad. Sci., vol. 90, Nov. 1993, pp. 10700-10704.

Sprenger et al., "Cyclobutendiylium-Farbstoffe", Angewandte Chemie., vol. 80, No. 14, 1968, pp. 541-546 (English Abstract Submitted).

Sprenger et al., "Das Cyclobuten-Diylium-Kation, Ein Neuartiger Chromophor Aus Quadratsaure", Angew. Chem., vol. 79, No. 12, 1967, 2 pages (English Abstract Submitted).

International Preliminary Report on Patentability received for PCT Patent Application No. PCT/US2014/028246, dated Sep. 24, 2015, 8 pages.

U.S. Appl. No. 15/460,657, filed Mar. 16, 2017, titled "Methods and Systems for Image Differentiated Multiplex Assays", (Copy Not Attached).

Written Opinion received for PCT Patent Application No. PCT/US2014/028246, dated Aug. 11, 2014, 6 pages.

Office Action received for Chinese Patent Application No. 201480010176.3, dated Mar. 2, 2018, 29 pages (20 pages of English Translation and 9 pages of Official Copy).

Tsao et al., U.S. Appl. No. 15/836,809, filed Dec. 8, 2017, titled "Image Differentiated Multiplex Assays for Multiplex Detection of DNA Mutations". (U.S. Patent Application is not submitted herewith pursuant to the waiver of 37 C.F.R. § 1.98(a)(2)(iii) issued by the Office on Sep. 21, 2004).

Tsao et al., U.S. Appl. No. 15/838,331, filed Dec. 11, 2017, titled "Image Differentiated Multiplex Assays for Multiplex Detection of DNA Mutations". (U.S. Patent Application is not submitted herewith pursuant to the waiver of 37 C.F.R. § 1.98(a)(2)(iii) issued by the Office on Sep. 21, 2004.).

Tsao et al., U.S. Appl. No. 16/332,271, filed Mar. 11, 2019, titled "Methods and Systems for Multiplex Assays", (U.S. Patent Application is not submitted herewith pursuant to the waiver of 37 C.F.R. § 1.98(a)(2)(iii) issued by the Office on Sep. 21, 2004.).

Tsao et al., U.S. Appl. No. 16/386,087, filed Apr. 16, 2019, titled "Image Differentiated Multiplex Assays", (U.S. Patent Application is not submitted herewith pursuant to the waiver of 37 C.F.R. § 1.98(a)(2)(iii) issued by the Office on Sep. 21, 2004.).

Tsao et al., U.S. Appl. No. 16/386,092, filed Apr. 16, 2019, titled "Image Differentiated Multiplex Assays", (U.S. Patent Application is not submitted herewith pursuant to the waiver of 37 C.F.R. § 1.98(a)(2)(iii) issued by the Office on Sep. 21, 2004.).

* cited by examiner

| Beads No. | Beads Type | Beads Description | Criteria | Result |
|---|---|---|---|---|
| 3023 | Kit ID (internal PC) | Demo Kit | TNFa >1000 | PASS |
| 3024 | Lot No. (internal NC) | PB031313-1 | IL6 <500 | PASS |
| 3025 | | | | |
| 4013 | Patient ID | 116707189 | | |
| 3080 | Testing Lab | PlexBio | | |

FIG. 2A

| Data Results: | |
|---|---|
| Well Type: | Standard |

| Beads Description | TNFa | IL-6 |
|---|---|---|
| Beads Type | Analyte | Analyte |
| Beads No. | 1011 | 1012 |

| Well ID | Exp Conc. (pg/ml) | MFI | MFI |
|---|---|---|---|
| A1 | 40000 | 35710 | 24771 |
| B1 | 10000 | 24199 | 24776 |
| C1 | 2500 | 9350 | 21486 |
| D1 | 625 | 2629 | 8955 |
| E1 | 156.25 | 749 | 3015 |
| F1 | 39.06 | 400 | 1669 |
| G1 | 9.77 | 324 | 1463 |
| H1 | 2.44 | 262 | 1091 |

FIG. 2B

| Well Type: | Sample | |
|---|---|---|
| Beads Description | TNFa | IL-6 |
| Beads Type | Analyte | Analyte |
| Beads No. | 1011 | 1012 |
| Well ID | MFI | MFI |
| A2 | 14421 | 2770 |

FIG. 2C

METHODS AND SYSTEMS FOR MULTIPLEX ASSAYS

CROSS-REFERENCE TO RELATED APPLICATIONS

This application claims priority to U.S. Provisional Patent Application No. 61/791,684, filed Mar. 15, 2013; the disclosure of which is hereby incorporated herein by reference in its entirety.

TECHNICAL FIELD

This application pertains to compositions comprising beads encoded with unique identifiers as well as methods of making and using the same in multiplex chemical and biological assays.

BACKGROUND

Immunological and molecular diagnostic assays play a critical role both in the research and clinical fields. Often it is necessary to perform assays for a panel of multiple targets to gain meaningful or bird's-eye view results to facilitate research or clinical decision-making. This is particularly true in the era of genomics and proteomics, where an abundance of genetic markers and/or biomarkers are thought to influence or be predictive of particular disease states. In theory, assay of multiple targets can be accomplished by testing each target separately in parallel or sequentially in different reaction vessels (i.e., multiple singleplexing). However, not only are assays adopting a singleplexing strategy often cumbersome, but they also typically required large sample volumes, especially when the targets to be analyzed are large in number.

A multiplex assay simultaneously measures multiple analytes (two or more) in a single assay. Multiplex assays are commonly used in high-throughput screening settings, where many specimens can be analyzed at once. It is the ability to assay many analytes simultaneously and many specimens in parallel that is the hallmark of multiplex assays and is the reason that such assays have become a powerful tool in fields ranging from drug discovery to functional genomics to clinical diagnostics. In contrast to singleplexing, by combining all targets in the same reaction vessel, the assay is much less cumbersome and much easier to perform since only one reaction vessel is handled per sample. The required test samples can thus be dramatically reduced in volume, which is especially important when samples (e.g., tumor tissues, cerebral spinal fluid, or bone marrow) are difficult and/or invasive to retrieve in large quantities. Equally important is the fact that the reagent cost can be decreased and assay throughput increased drastically.

Many technologies for multiplex detection are available, including fluorescent-coded beads, barcoded magnetic beads, etc. Traditionally, all these suspension array beads are utilized for performing the actual bioassays. In these bead-based multiplex assay systems, there are two identification systems for every bead in the assay. One system is for the identification of the capture agent attached to the surface of the beads while the second identification system is used to indicate the presence or quantity of the analyte that binds to the particular capture agent. The Luminex technology is an example of a bead-based multiplex detection system centered on latex beads that have two different fluorophores associated with any given bead. The first fluorescent dye is injected into the beads during the latex polymerization process and is used to reveal the identity of the beads (i.e. the identification of the capture agent associated with the bead). The second fluorophore is conjugated to an analyte binder introduced to the beads when there is an analyte molecule captured by the bead-linked analyte capture agent. In other bead-based assays, the first identification system can be replaced by systems other than those which are fluorescence-based. For example, in Applied Biocode's BMB system, the first identification system is replaced by a barcode.

In spite of these advances, there remains a need for methods and systems utilizing individually identifiable beads for use in multiplex high-throughput assays that not only ensure high precision and reproducibility of experimental results, but which also are capable of performing other functions related to information and data storage that are not directly related to the assays per se.

Throughout this specification, various patents, patent applications and other types of publications (e.g., journal articles) are referenced. The disclosure of all patents, patent applications, and publications cited herein are hereby incorporated by reference in their entirety for all purposes.

SUMMARY OF THE INVENTION

The invention provided herein discloses, inter alia, compositions of beads (such as, polymeric beads) of substantially identical size and shape encoded with unique information-storing identifiers and methods for use of the same in multiplex chemical and biological assays.

Accordingly, provided herein are methods for conducting a multiplex assay comprising the steps of: a) contacting a sample with beads in an assay system, wherein each bead in the system comprises an identifier; wherein the system comprises (i) at least one bead with an identifier that is recognized by an imaging processor as a specific assay, and (ii) a plurality of beads, wherein each bead comprises a capture agent immobilized on the surface of the bead that specifically binds to an analyte; and simultaneously or sequentially, in any order: b) identifying the identifier that is recognized by the imaging processor as the specific assay; and c) detecting the binding of the analyte in the sample by analyzing the binding of the analyte to the capture agent immobilized on the surface of the bead based on the identification of the identifier as the specific assay. In some embodiments, the system further comprises (iii) at least one bead with an identifier that is recognized by the imaging processor as corresponding to a manufacturing lot. In some embodiments, the identifier that is recognized by the imaging processor as corresponding to a manufacturing lot is additionally recognized by the imaging processor as identifying the bead as a positive or negative control. In some embodiments, the system further comprises (iii) at least one bead with an identifier that is recognized by the imaging processor as corresponding to an individual. In some embodiments, the system further comprises (iii) at least one bead with an identifier that is recognized by the imaging processor as corresponding to a location. In some embodiments, the locational identifier corresponds to a hospital, a diagnostic laboratory, an address, a health care professional's office, or a research laboratory. In some embodiments, the system further comprises (iii) at least one bead that is pre-labeled for calibration of the imaging processor. In some embodiments, the system further comprises (iii) at least one bead that is pre-labeled for monitoring functions of the imaging processor. In some embodiments, the identifier is an encoded pattern or a combination of encoded patterns, an RFID signal, or a fluorescent gradient. In some embodiments, the beads comprise a spherical or rectangular shape. In some embodiments, the beads are less than about 300 μm in diameter. In some embodiments, the surface of the bead is smooth and lacks surface irregularities. In some embodiments, the surface of the bead comprises at least one site for chemical attachment of the capture agent. In some embodiments, the capture agent is selected from the group consisting of: a DNA molecule, a DNA-analog-molecule, an RNA-molecule, an RNA-analog-molecule, a polynucleotide, a protein, an enzyme, a lipid, a phospholipid, a carbohydrate moiety, a polysaccharide, an antigen, a virus, a cell, an antibody, and an antibody fragment. In some embodiments, the plurality of beads are magnetic or non-magnetic.

Additionally, provided herein are kits for conducting a multiplex assay comprising: at least one bead with an identifier that is recognized by an imaging processor as a specific assay; and one or more of a) a plurality of beads, wherein each bead comprises i) an identifier, and ii) a capture agent immobilized on the surface of the bead that specifically binds to an analyte, wherein the identifier corresponds to the capture agent; b) a signal-emitting entity capable of directly or indirectly binding to the analyte or capture agent; c) at least one bead with an identifier that is recognized by the imaging processor as corresponding to a manufacturing lot; d) at least one bead with an identifier that is recognized by the imaging processor as corresponding to an individual; e) at least one bead with an identifier that is recognized by the imaging processor as corresponding to a locational identifier; or f) at least one bead that is pre-labeled for calibration of the imaging processor. In some embodiments, the signal-emitting entity indirectly binds to the analyte or capture agent via a secondary antibody that is conjugated to the signal-emitting entity. In some embodiments, the signal-emitting entity indirectly binds to the analyte or capture agent via a nucleotide probe that is conjugated to the signal-emitting entity. In some embodiments, the signal-emitting entity is phycoerythrin, GFP, RFP, CFP, YFP, FITC, horseradish peroxidase, alkaline phosphatase, or a radiolabel. In some embodiments, the kit further comprises g) an imaging processor for (i) identifying the at least one bead with an identifier that is recognized by the imaging processor as a specific assay, (ii) identifying the identifier on the plurality of beads in a), (iii) detecting the amount of signal produced by the signal-emitting entity of b), (iv) identifying the at least one bead with an identifier that is recognized by the imaging processor as a manufacturing lot in c), (v) identifying the at least one bead with an identifier that is recognized by the imaging processor as an individual in d), (vi) identifying the at least one bead with an identifier that is recognized by the imaging processor as a locational identifier in e), or (vii) identifying the at least one bead that is pre-labeled for calibration of the imaging processor in f). In some embodiments, the kit further comprises h) an entity capable of directly or indirectly binding to the analyte or capture agent, wherein the entity comprises an affinity tag. In some embodiments, the affinity tag is biotin, His6, or maltose. In some embodiments of any of the embodiments described herein, the kit further comprises i) at least one bead that is pre-labeled for monitoring functions of the imaging processor. In some embodiments, the identifier is an encoded pattern or a combination of encoded patterns, an RFID signal, or a fluorescent gradient. In some embodiments, the beads comprise a spherical or rectangular shape. In some embodiments, the beads are less than about 300 μm in diameter. In some embodiments, the surface of the bead is smooth and lacks surface irregularities. In some embodiments, the surface of the bead comprises at least one site for chemical attachment of the capture agent. In some embodiments, the capture agent is selected from the group consisting of: a DNA molecule, a DNA-analog-molecule, an RNA-molecule, an RNA-analog-molecule, a polynucleotide, a protein, an enzyme, a lipid, a phospholipid, a carbohydrate moiety, a polysaccharide, an antigen, a virus, a cell, an antibody, a small molecule, and an antibody fragment. In some embodiments, the plurality of beads are magnetic.

Additionally, provided herein are multiplex assay systems comprising: a) a plurality of beads in the kit of any one of the embodiments described herein; and b) an apparatus comprising an imaging processor system and a reaction detection system, wherein the identification of an identifier that corresponds to one or more of i) a specific assay, (ii) a specific analyte, (iii) a manufacturing lot, (iv) an individual, (v) a locational identifier, and/or (vi) a calibration signal by the imaging processor in the decoding system activates the use of a software analyzing detection signals detected by reaction detection system correlated to the specific assay.

BRIEF DESCRIPTION OF THE DRAWINGS

FIGS. 2A-2C show the results of an exemplary multiplex biological assay.

DETAILED DESCRIPTION

Figure 1:
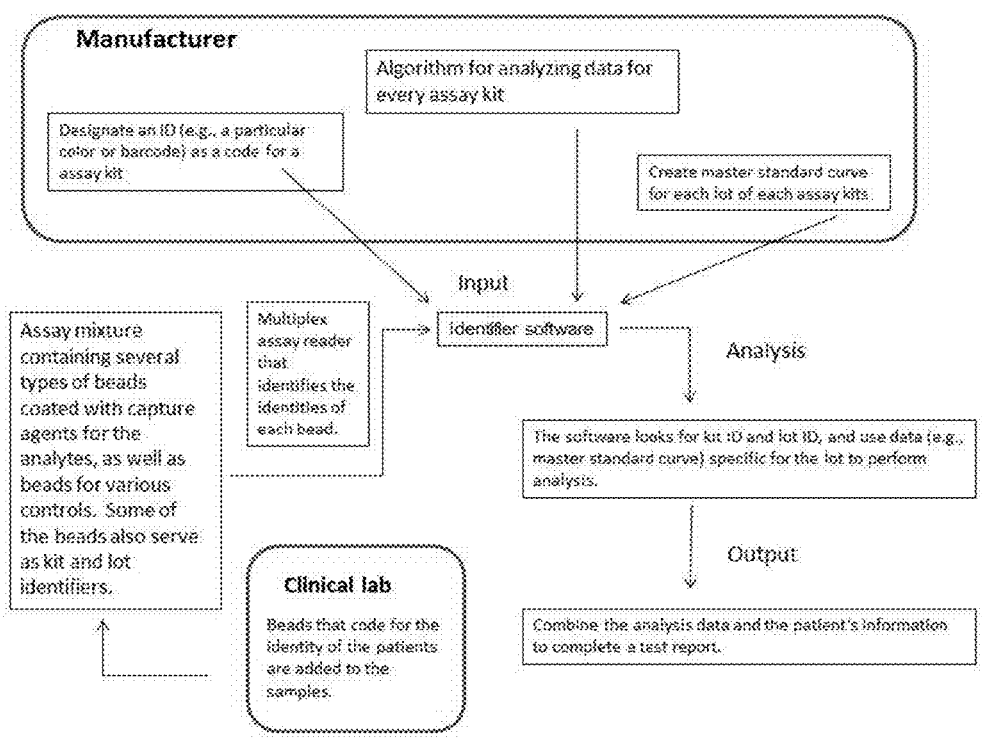
FIG. 1 depicts an exemplary method for use of the bead compositions encoded with unique identifiers described herein.

This invention provides, inter alia, bead (such as, polymeric bead) compositions for use in multiplex biological and chemical assays as well as methods of making and using the same. Each individual bead in a composition possesses a unique identifier and specific capture agents (for example, chemical compounds and/or biomolecules) can be attached to the surface of each bead. Such beads are therefore useful for conducting high throughput and multiplex chemical and biological assays, since, by virtue of each bead containing a unique identifier, the identity of any individual capture agent attached to the bead can be readily ascertained. These beads and/or additional beads in the composition can further be labeled with identifiers for purposes of specific information storage including, but not limited to, identification of the manufacturing lot number for the beads, identification of the assay for which the beads will be used, identification of a location (such as, but not limited to, the origin of a sample used in an assay or the lab or hospital where the assay was conducted), and/or identification of an individual (such as, but not limited to, an individual who supplied a given sample to be assayed). Additional beads in the composition can be labeled with identifiers for purposes of calibrating an imaging processor used to identify the identifier associated with each bead in the composition.

I. General Techniques

The practice of the invention will employ, unless otherwise indicated, conventional techniques in polymer technology, photolithography, microfluidics, organic chemistry, biochemistry, oligonucleotide synthesis and modification, bioconjugate chemistry, nucleic acid hybridization, molecular biology, microbiology, genetics, recombinant DNA, and related fields as are within the skill of the art. The techniques are described in the references cited herein and are fully explained in the literature.

For molecular biology and recombinant DNA techniques, see, for example, (Maniatis, T. et al. (1982), *Molecular Cloning: A Laboratory Manual*, Cold Spring Harbor; Ausubel, F. M. (1987), *Current Protocols in Molecular Biology*, Greene Pub. Associates and Wiley-Interscience; Ausubel, F. M. (1989), *Short Protocols in Molecular Biology: A Compendium of Methods from Current Protocols in Molecular Biology*, Greene Pub. Associates and Wiley-Interscience; Sambrook, J. et al. (1989), *Molecular Cloning: A Laboratory Manual*, Cold Spring Harbor; Innis, M. A. (1990), *PCR Protocols: A Guide to Methods and Applications*, Academic Press; Ausubel, F. M. (1992), *Short Protocols in Molecular Biology: A Compendium of Methods from Current Protocols in Molecular Biology*, Greene Pub. Associates; Ausubel, F. M. (1995), *Short Protocols in Molecular Biology: A Compendium of Methods from Current Protocols in Molecular Biology*, Greene Pub. Associates; Innis, M. A. et al. (1995), *PCR Strategies*, Academic Press; Ausubel, F. M. (1999), *Short Protocols in Molecular Biology: A Compendium of Methods from Current Protocols in Molecular Biology*, Wiley, and annual updates.

For DNA synthesis techniques and nucleic acids chemistry, see for example, Gait, M. J. (1990), *Oligonucleotide Synthesis: A Practical Approach*, IRL Press; Eckstein, F. (1991), *Oligonucleotides and Analogues: A Practical Approach*, IRL Press; Adams, R. L. et al. (1992), *The Biochemistry of the Nucleic Acids*, Chapman & Hall; Shabarova, Z. et al. (1994), *Advanced Organic Chemistry of Nucleic Acids*, Weinheim; Blackburn, G. M. et al. (1996), *Nucleic Acids in Chemistry and Biology*, Oxford University Press; Hermanson, G. T. (1996), *Bioconjugate Techniques*, Academic Press).

For microfabrication, see for example, (Campbell, S. A. (1996), *The Science and Engineering of Microelectronic Fabrication*, Oxford University Press; Zaut, P. V. (1996), *Micromicroarray Fabrication: a Practical Guide to Semiconductor Processing*, Semiconductor Services; Madou, M. J. (1997), *Fundamentals of Microfabrication*, CRC Press; Rai-Choudhury, P. (1997). Handbook of Microlithography, Micromachining, & Microfabrication: Microlithography).

II. Definitions

As used herein, the singular form "a", "an", and "the" includes plural references unless indicated otherwise.

As used herein, "biomolecule" means any molecule that is produced by a living organism, including, but not limited to, large polymeric molecules such as proteins, polysaccharides, lipids, and nucleic acids as well as small molecules such as, but not limited to, primary metabolites, secondary metabolites, and natural products.

As used herein, "sample" refers to a composition containing a material, such as a molecule, to be detected. In one embodiment, the sample is a "biological sample" (i.e., any material obtained from a living source (e.g. human, animal, plant, bacteria, fungi, protist, virus)). The biological sample can be in any form, including solid materials (e.g. tissue, cell pellets and biopsies) and biological fluids (e.g. urine, blood, saliva, lymph, tears, sweat, prostatic fluid, seminal fluid, semen, bile, mucus, amniotic fluid and mouth wash (containing buccal cells)). Solid materials typically are mixed with a fluid. Sample can also refer to an environmental sample such as water, air, soil, or any other environmental source.

"Analyte," as used herein, is a broad term and is used in its ordinary sense as a substance the presence, absence, or quantity of which is to be determined, including, without limitation, to refer to a substance or chemical constituent in a sample such as a biological sample or cell or population of cells that can be analyzed. An analyte can be a substance for which a naturally occurring binding member exists, or for which a binding member can be prepared. Non-limiting examples of analytes include, for example, antibodies, antigens, polynucleotides (such as RNA, DNA, or cDNA), polypeptides, proteins, hormones, cytokines, growth factors, steroids, vitamins, toxins, drugs, and metabolites of the above substances, as well as bacteria, viruses, fungi, algae, fungal spores and the like.

As used herein, a "biological sample" refers to material that can be derived from a living source. Such samples include, biomolecules and biopolymers.

As used herein, the term "chemical compound" means any chemical substance consisting of two or more different chemical elements with a unique and defined chemical structure.

It is understood that aspects and embodiments of the invention described herein include "comprising," "consisting," and "consisting essentially of" aspects and embodiments.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

III. Bead Compositions

Provided herein are compositions comprising a plurality of beads (such as, polymeric beads) of substantially identical size and shape. In some embodiments, each bead (such as, a polymeric bead) can measure no more than about 1 mm, about 750 µm, about 500 µm, about 400 µm, about 300 µm, about 250 µm, about 200 µm, about 175 µm, about 150 µm, about 125 µm, about 100 µm, about 90 µm, about 80 µm, about 70 µm, about 60 µm, about 50 µm, about 40 µm, about 30 µm, about 20 µm, or about 10 µm at its widest dimension, inclusive, including every value in between these numbers. An identifier can be embedded within or attached to or etched upon the material comprising each bead (such as, polymeric bead) making individual bead identifiable based on decoding the identifier. In some embodiments, the identifier is an encoded pattern or a combination of encoded patterns (such as a barcode), a radio frequency (such as a radio frequency identification (RFID) signal), or a fluorescent gradient. In some embodiments, the beads (such as, polymeric beads) can include a paramagnetic material (such as a ferromagnetic material) that results in the attraction of the plurality of beads to a magnet when an external magnetic field is applied in the vicinity of the beads. Suitable ferromagnetic materials can include, but are not limited to, iron, nickel, cobalt, and alloys of rare earth metals.

The compositions described herein can contain any number of beads (such as, polymeric beads), including more than 2, more than 20, more than 30, more than 40, more than 50, more than 60, more than 70, more than, 80, more than 90, or more than 100 beads, inclusive, as well as any numerical value in between these numbers. In other embodiments, the compositions described herein can have more than $10^2$, more than $10^3$, more than $10^4$, more than $10^5$, more than $10^6$, more than $10^7$, more than $10^8$, more than $10^9$, more than $10^{10}$, more than $10^{11}$, or more than $10^{12}$ beads, inclusive, as well as any numerical value in between these numbers.

A. Shape of the Beads

The beads described herein can possess any three dimensional geometric shape. In some embodiments, the plurality of beads can be spherical, including semi-spherical, in shape. In other embodiments, the plurality of beads can be ovoid in shape. In some embodiments, the plurality of beads can be cubical in shape including, but not limited to, rectified cubes, rectangular cubes, truncated cubes, cantellated cubes, omnitruncated cubes, or snub cubes. In some embodiments, the plurality of beads can be cylindrical in shape including, but not limited to, right circular cylinders, elliptic cylinders, or oblique cylinders. In some embodiments, the plurality of beads can be conic in shape including, but not limited to, right circular cones or oblique circular cones. In some embodiments, the plurality of beads can be pyramidal in shape including, but not limited to, square pyramids or pentagonal pyramids. In some embodiments, the plurality of beads can be tetrahedral in shape. In some embodiments, the plurality of beads can be prismic in shape. Additionally, other embodiments of the plurality of beads can be any form of polyhedron including, but not limited to, dodecahedrons, icosidodecahedrons, rhombic triacontahedrons, or rhombic dodecahedrons.

In some aspects, the beads of some of the compositions described herein can have surfaces that are smooth and lack surface irregularities. As used herein, a bead is "smooth and lacks surface irregularities" if the distance from the gravitational center of any one bead in the composition to any two points on the surface of the bead varies by no more than about 10%. In some embodiments, the distance from the gravitational center of any one bead (such as, a polymeric bead) in the composition to any two points on the surface of the bead can vary by no more than about 19%, about 18%, about 17%, about 16%, about 15%, about 14%, about 13%, about 12%, about 11%, about 10%, about 9%, about 8%, about 7%, about 6%, about 5%, about 4%, about 3%, about 2%, about 1%, about 0.5%, or about 0.25%, inclusive, as well as any numerical value in between these percentages. In some embodiments, microscopic examination can be used to determine that the bead surface is free from deep dents, holes, or high bumps.

B. Size of the Beads

In some aspects, the beads (such as polymeric beads) of the compositions described measure no more than about 300 µm at their widest dimension. In some embodiments, each bead measures no more than about 1 mm, about 750 µm, about 500 µm, about 400 µm, about 300 µm, about 250 µm, about 200 µm, about 175 µm, about 150 µm, about 125 µm, about 100 µm, about 90 µm, about 80 µm, about 70 µm, about 60 µm, about 50 µm, about 40 µm, about 30 µm, about 20 µm, or about 10 µm at its widest dimension, inclusive, including every value in between these numbers. In some embodiments, the beads of some of the compositions described herein can be spherical and measure about 300 µm in diameter. In other embodiments, the beads of some of the compositions described herein can be rectangular and measure about 300 µm in diameter. In other embodiments, the beads of some of the compositions described herein can be rectangular and measure about 40×60×5 µm.

In some aspects, the beads of the compositions described herein can be of substantially identical size and shape. As used herein, "substantially identical size" means that the variation between the distances measured at the widest dimension between any two beads (such as, polymeric beads) in a composition is less than about 10%. In some embodiments, the variation between the distances measured at the widest dimension between any two beads in a composition can be less than about 9%, about 8%, about 7%, about 6%, about 5%, about 4%, about 3%, about 2%, about 1%, about 0.5%, or about 0.25%, inclusive, as well as any numerical value in between these numbers. "Substantially identical shape," as used herein, means that each bead of a composition is the same shape as any other bead within the composition.

C. Identifiers

Each bead in the bead compositions described herein is associated with one or more unique identifiers. The identifier can be any discrete mark, code (such as a bar code), or signal (such as a fluorescent dye or a radio wave emitted by an RFID chip) that is physically associated (such as by etching, being embedded within, or physical attachment) with an individual bead in a composition. In some aspects, the identifier corresponds to the identity of a capture agent immobilized to the surface of the bead (e.g., an antibody, a small molecule chemical compound, or a nucleic acid probe) for purposes of conducting a specific assay. In other aspects, the bead compositions described herein contain additional beads with identifiers that can also be utilized for storing information (e.g., data) and/or performing other functions that are not directly related to the multiplex assays per se. In one embodiment, the bead (such as, polymeric bead) compositions described herein contain at least one bead with an identifier that is recognized by an imaging processor as corresponding to a particular biological or chemical multiplex assay. The assay identifier can also be used to store information related to a particular multiplex assay kit, including the function of all of the other beads in a composition contained within the kit (such as, but not limited to, the identity of capture agents associated with the beads in the composition or beads labeled with identifiers for purposes of calibrating the imaging processor used in conjunction with the assay).

In another embodiment, the bead compositions described herein contain at least one bead with an identifier that is recognized by an imaging processor as corresponding to a particular manufacturing lot. The lot identifier can be used to store information related to the particular manufacturing lot of an assay kit, including the date of manufacture, expiration date, and external standard curves which can be used for calculating the concentration of one or more target analytes in a sample (such as a biological sample) to be assayed. In a further embodiment, external standard curves for each target analyte in a multiplex assay kit can be determined for each production lot and the data incorporated into software accompanying the multiplex assay kit each time a new manufacturing lot is produced. In yet another embodiment, data related to these pre-determined standard curves can be accessible over the internet by the imaging processor which can use them to calculate the concentration of one or more target analytes in a sample (such as a biological sample).

In other embodiments, the bead (such as, polymeric bead) compositions described herein contain at least one bead with an identifier that is recognized by an imaging processor as corresponding to an individual. The individual identifier can be used to store information related to, for example, individuals submitting samples for biological or chemical assay analysis or individuals ordering those assays to be performed, such as, but not limited to, a health care professional. As used herein, an "individual" can be a mammal, such as any common laboratory model organism. Mammals include, but are not limited to, humans and non-human primates, farm animals, sport animals, pets (such as dogs or cats), mice, rats, and other rodents. In some embodiments, an individual is a human. In other embodiments, an individual is a patient who has provided a biological sample to be biologically or chemically assayed. In another embodiment, an individual is a health care professional who ordered an assay to be performed. In yet another embodiment, the individual is a governmental agency or department.

In other embodiments, the bead compositions described herein contain at least one bead with an identifier that is recognized by an imaging processor as corresponding to a location. The locational identifier can be used to store information related to locations related to the samples to be assayed or the location of the source of the samples to be assayed. Non-limiting examples of locational identifiers include hospitals, the offices of health care professionals, an address (such as the address of an individual, a hospital, or a health care professional), or a laboratory (such as a diagnostic laboratory, a medical laboratory, a university laboratory, or a research laboratory).

In other embodiments, the bead compositions described herein contain at least one bead with an identifier that is recognized by an imaging processor as corresponding to a temporal identifier. Non-limiting examples of temporal identifiers include the date of specimen collection.

In another embodiment, the bead compositions described herein contain at least one bead with an identifier that is recognized by an imaging processor as identifying the bead as a positive or negative control bead. The positive control bead may be, for example, a bead coated with biotinylated bovine serum albumin (BSA), or any other marker that may be used as a positive control. The negative control bead may be, for example, a bead coated with BSA, or any other marker that may be used as a negative control.

In another embodiment, the bead compositions described herein contain at least one bead that is pre-labeled for calibration of the imaging processor.

In some embodiments, the bead compositions described herein contain at least one bead with an identifier that is recognized by an imaging processor as corresponding to more than one function or piece of information (such as but not limited to the particular biological or chemical multiplex assay, information related to a particular multiplex assay kit, information related to the particular manufacturing lot, an individual, a location). For example, the bead compositions described herein may contain at least one bead with an identifier that is recognized by an imaging processor as corresponding to information regarding the manufacturing lot (including but not limited to the manufacturing date, expiration date, standard curves, and cut off values) as well as identifying the bead as a negative control bead. As another example, the bead compositions described herein may contain at least one bead with an identifier that is recognized by an imaging processor as corresponding to information regarding the assay kit (including but not limited to the function of all of the other beads in the composition contained within the kit) as well as identifying the bead as a positive or negative control. As another example, the bead compositions described herein may contain at least one bead with an identifier that is recognized by an imaging processor as corresponding to information regarding the manufacturing lot (including, but not limited to, the date of manufacture, expiration date, and external standard curves which can be used for calculating the concentration of one or more target analytes in a sample to be assayed) as well as identifying the bead as a positive or negative control. As another example, the bead compositions described herein may contain at least one bead with an identifier that is recognized by an imaging processor as corresponding to the patient name and identifier, the hospital, the health care professional, the diagnostic laboratory, and the date of specimen collection. As yet another example, the bead compositions described herein may contain at least one bead with an identifier that is recognized by an imaging processor as identifying the capture agent that is bound to the surface of the bead and as corresponding to information regarding the assay kit (including but not limited to the function of all of the other beads in the composition contained within the kit).

D. Beads with Encoded Patterns

In some aspects, the identifier associated with any of the bead compositions described herein is an encoded pattern or a combination of encoded patterns. In one embodiment, the encoded pattern is a bar code. The encoded pattern associated with each bead (such as, a polymeric bead) can be decoded by an imaging processor to identify a capture agent that is bound to the surface of a particular bead in the plurality of beads. In other embodiments, the encoded pattern associated with a bead in the plurality of beads can be decoded by an imaging processor to identify other sources of information about the particular assay being conducted. These can include, but are not limited to, the identity of the assay, the manufacturing lot of the plurality of beads, a locational identifier (such as, but not limited to, the location of a hospital, a doctor's office, or a laboratory). Further encoded patterns associated with each bead can be pre-labeled for calibration of the imaging processor. In other embodiments, the encoded pattern associated with a bead in a plurality of beads can be decoded by an imaging processor to identify more than one type of information, such as those discussed above.

Individual beads can be identified by marking them with an encoded pattern comprising a high contrast and high signal-to-noise barcode image to facilitate identification by an image processor. The image is implemented by a physical structure having a pattern that is partially substantially transmissive (e.g., transparent, translucent, and/or pervious to light), and partially substantially opaque (e.g., reflective and/or absorptive to light) to light. The pattern of transmitted light is determined (e.g., by scanning or imaging), and the code represented by the image on the coded bead can be decoded. Various barcode patterns, such as circular, square, or other geometrical shapes, can be designed as long as it represents a "1" or "0" and can be recognized by the image processor. In one embodiment, at least about 10 patterns can be provided on the bead (such as, a bead) to encode 10 bits to 12 bits or more, allowing 1,024 to 4,096 or more unique identifiers.

In one embodiment, the bar-coded bead comprises a generally rectangular body having a series of alternating light transmissive and opaque sections, with relative positions, widths and/or spacing resembling a 1D or 2D bar code image (e.g., a series of narrow slits (e.g., about 1 to 5 microns in width) representing a "0" code and wide slits (e.g., about 1 to 10 microns in width) representing a "1" code, or vice versa, to form a binary code). In another embodiment, the bar-coded bead has a shape of a flat pallet or disc. The body of the coded bead can be configured to have at least two orthogonal cross sections that are different in relative geometry and/or size. Further, the geometry of the cross sections can be symmetrical or non-symmetrical, and/or regular or irregular shape. In this particular embodiment, all three orthogonal axes are of different lengths, and the geometries of all three orthogonal cross sections are symmetrical and of regular shape.

In a further aspect, the structure defining the barcode can be detected by the image processor without considering the boundaries of the beads. In one embodiment, this approach of decoding is best implemented with "positive" type barcodes, instead of the "negative" type described above in which slits are used to define the barcodes in an opaque background of the beads. Positive barcodes are defined by opaque bars (e.g., defined by reflective surfaces) in a transparent background.

To decode an encoded barcode pattern identifier on the surface of a bead, the alternating transmissive and opaque sections of the bead are scanned with light or imaged by the imaging processor to determine the code that is represented by the image or that is determined from the transmitted light. In some embodiments, a series of signal pulses representing the detection of light transmitted by the imaging processor are obtained. The signal pulses correspond to the contrast of transmitted versus blocked light across the longitudinal axis of the barcoded bead. In one embodiment, the width of each signal pulses represents a "1" or a "0" in the code. In one non-limiting example, the wider pulses represent 1's and the narrow pulses represent 0's. The relative positions of the slits on the bead determine which of the bits is the least significant bit (LSB) or the most significant bit (MSB). In one embodiment, the least significant bit can be placed closer to one edge or end of the bead to distinguish it from the most significant bit at the opposing edge or end.

The bar-coded bead (such as, a polymeric bead) can be fabricated using conventional methods used in thin film formation in a clean room microfabrication facility. The structure of the bar-coded bead can be obtained using processes that can include conventional photo-lithography, printing, silk-screening, curing, developing, etching (e.g., chemical etching, ion etching, and/or other removing processes), plating, dicing, and other process steps well known in the art for such types of structure and the material involved.

In one embodiment, the process for forming the barcoded bead can include first forming a first photopolymer layer, then forming a metal layer followed by etching the slits which comprise the barcode therein. A second photopolymer layer can then be formed on the metal layer, which fills the slits. In an alternative embodiment, the slits can be filled with another transparent material, before forming the second photopolymer layer. With this embodiment, surface conditions can be made the same for both exposed planar surfaces of the bar-coded bead, to provide similar surface coating and immobilization conditions. Another embodiment is to coat the bar-coded bead with polymer or functional molecules, such as biotin, carboxylated, or streptavidin; therefore, the whole bead has the same condition for molecular immobilization of a capture agent.

In another embodiment, the barcoded beads (such as, polymeric beads) have additional surface functional groups, such as carboxylates, esters, alcohols, carbamides, aldehydes, amines, sulfur oxides, nitrogen oxides, or halides. The functionality of the beads' surface groups gives the bead their coupling capability allowing chemical binding of capture agent. These functional groups are useful for attachment of capture agents, such as, but not limited to, antibodies, antigens, nucleic acid probes, or small molecule chemical compounds. These can also include reactants that can form specific, high-affinity conjugates such as, but not limited to, avidin-biotin, receptor-ligand, ligand-ligate, enzyme-substrate, lectin-carbohydrate, or protein A-immunoglobulin In a further embodiment, a paramagnetic material can be embedded in the intermediate layer in the barcoded bead, and thus sandwiched between the first layer and second layer of polymer films. Paramagnetic materials include magnesium, molybdenum, lithium, aluminum, nickel, tantalum, Fe203, and Fe304. It is noted that the paramagnetic material on the barcoded bead would also function as a light blocking material, so a reflective layer is not necessary. The present invention would allow decoding based on transmitted light, even in the presence of the paramagnetic material. Additional sources of information for fabrication of barcoded beads can be found in U.S. Patent Application Publication No. US 2011/0007955, the disclosure of which is incorporated by reference herein in its entirety.

E. Fluorescently Coded Beads

In some aspects, the identifier associated with any of the bead (such as, polymeric bead) compositions described herein is a fluorescent dye having a particular wavelength. In some embodiments, the fluorescent dye is injected into the bead. The wavelength of the fluorescent dye associated with each bead can be decoded by an imaging processor to identify a capture agent that is bound to the surface of a particular bead in the plurality of beads. In other embodiments, the wavelength of the fluorescent dye associated with a bead in the plurality of beads can be decoded by an imaging processor to identify other sources of information not strictly related to assay being conducted per se. These can include, but are not limited to, the identity of the assay, the manufacturing lot of the plurality of polymeric beads, or a locational identifier (such as, but not limited to, the location of a hospital, a doctor's office, or a laboratory). In another embodiment, further fluorescent dye-produced wavelengths associated with a bead in the plurality of beads can be pre-labeled for calibration of the imaging processor. In other embodiments, the wavelength of the fluorescent dye associated with a bead in a plurality of beads can be decoded by an imaging processor to identify more than one type of information, such as those disclosed above.

The fluorescent dye-associated polymeric beads can be made of any polymeric material, such as, but not limited to, polystyrene or latex. Other non-limiting examples of types of polymers suitable for fabrication of fluorescent dye-associated polymeric beads include brominated polystyrene, polyacrylic acid, polyacrylonitrile, polyacrylamide, polyacrolein, polybutadiene, polydimethylsiloxane, polyisoprene, polyurethane, polyvinylacetate, polyvinylchloride, polyvinylpyridine, polyvinylbenzylchloride, polyvinyltoluene, polyvinylidene chloride, polydivinylbenzene, polymethylmethacrylate, or combinations thereof.

In another embodiment, the fluorescent dye-associated beads can also contain 1 to 30% (such as 1 to 25%, 1 to 20%, 1 to 15%, 1 to 10%, 1 to 5%, 4%, 3%, or 2%, inclusive, including percentages in between these values) of a cross-linking agent, such as divinyl benzene, ethylene glycol dimethacrylate, trimethylol propane trimethacrylate, or N,N' methylene-bis-acrylamide or other functionally equivalent agents known in the art.

In a further embodiment, the fluorescent dye-associated polymeric beads have additional surface functional groups, such as carboxylates, esters, alcohols, carbamides, aldehydes, amines, sulfur oxides, nitrogen oxides, or halides. The functionality of the polymeric beads' surface groups gives the polymeric bead their coupling capability allowing chemical binding of capture agent. In addition to functional groups on beads (such as, polymeric beads), the fluorescent dyes themselves can also carry chemically reactive functional groups, which in addition to groups listed above can also be carboxylic acid, carboxylic acid succinimidyl ester, carboxylic acid anhydride, sulfonyl chloride, sulfonyl fluoride, hydrazine derivatives, acyl azide, isocyanate, haloacetamide, phenols, thiols, and ketones. These functional groups are useful for attachment of capture agents, such as, but not limited to, antibodies, antigens, nucleic acid probes, or small molecule chemical compounds. These can also include reactants that can form specific, high-affinity conjugates such as, but not limited to, avidin-biotin, receptor-ligand, ligand-ligate, enzyme-substrate, lectin-carbohydrate, or protein A-immunoglobulin. For flow cytometry analysis, the capture agents are also commonly labeled with fluorescent tags or labels having a different wavelength than the fluorescent dye-associated with the polymeric bead, such as, but not limited to, fluorescein (FITC) or rhodamine. Further information related to the fabrication and use of fluorescent dye-associated polymeric beads can be found in U.S. Pat. No. 6,514,295, the disclosure of which is incorporated by reference herein in its entirety.

In one embodiment, suitable solvents can be selected based on their ability to solubilize a particular class of hydrophobic dyes for use in conjunction with the beads. These solvents can be acyl, aliphatic, cycloaliphatic, aromatic or heterocyclic hydrocarbons; the solvents may or may not have halogens, oxygen, sulfur, nitrogen, and/or phosphorous as either terminal groups or as integral parts of a ring or chain. Specifically, solvents such as toluene, xylene, hexane, pentane, acetone, DMSO, or methylene chloride can be used. In one embodiment, chlorinated solvents, for example, chloroform, are used to solubilize the squaric acid class of dyes, which is a non-limiting example of a dye that can be used in conjunction with the polymeric bead compositions of the invention.

In another embodiment, two fluorescent squaraine dyes can be used, e.g., a red dye such as 1,3-bis[(1,3-dihydro-1,3,3rimethyl-2H-indol-2-ylidene)methyl]-2,4-dihydroxycyclobutenediylium, bis(inner salt) and an orange dye such as 2-(3,5-dimethylpyrrol-2-yl)-4-(3,5-dimethyl-2H-pyrrol-2-ylidene)-3-hydroxy-2-cyclobuten-1-one. The molar ratio between first and second dye, when present in a polymeric bead, will preferably be between about 0 and 10,000, such as between 0.00001 and 2,000, 0.0001 and 2000, 0.001 and 2000, 0.01 and 2000, 0.1 and 2000, 1 and 2000, 10 and 2000, 100 and 2000, 1000 and 2000, 1000 and 3000, 2000 and 5000, 2000 and 6000, 2000, and 7000, 2000 and 9000, and 2000 and 10,000. Both dyes would preferably be excited at the same absorption wavelength, e.g., ranging from ultraviolet to about 800 nm, and emit fluorescent light at two distinct, essentially non-overlapping wavelengths distant from each other by at least 10 nm, (for example by at least any of 15 nm, 20 nm, 25 nm, 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 110 nm, 120 nm, 130 nm, 140 nm, 150 nm, 160 nm, 170 nm, 180 nm, 190 nm, 200 nm, 250 nm, 300 nm, 350 nm, 400 nm, 450 nm, 500 nm, 550 nm, 600 nm, 650 nm, 700 nm, 750 nm, or 800 nm, inclusive, including any wavelengths between these numbers). In some embodiments, a first fluorescent dye associated with at least one bead in a plurality of beads (such as, polymeric beads) serves as an identifier for the capture agent immobilized on the surface of a polymeric bead (such as any of the polymeric beads described herein) while a second fluorescent dye associated with at least one bead in the plurality of beads serves as a identifier for storing information not strictly related to conducting an assay such as, but not limited to, manufacturing lot number for the polymeric beads, identification of the assay for which the polymeric beads will be used, identification of a location, and/or identification of an individual, so long as each dye emits fluorescent light at two distinct, essentially non-overlapping wavelengths distant from each other by at least 10 nm.

Squaric acid based fluorescent dyes can be synthesized by methods described in the literature. See, for example, Sprenger et al. *Angew. Chem.*, 79, 581 (1967); *Angew. Chem.*, 80, 541 (1968); and Maaks et al, *Angew Chem. Intern. Edit.*, 5, 888 (1966), the disclosures of each of which are incorporated by reference. Briefly, one equivalent of squaric acid (1,2-dihydroxycyclobutenedione) is condensed with two equivalents of an active compound, such as a pyrrole, indoline, or aniline, and refluxed in a mixture of an alcohol and an aromatic solvent (such as benzene) under conditions that allow removal of water from the reaction mixture. The resulting dye can be collected and purified by a number of standard methods, such as recrystallization, distillation, chromatography, etc. Additionally, unsymmetrically substituted squaric acid compounds can be synthesized by methods such as those described by Law et al., *J. Org. Chem.* 57, 3278, (1992), the disclosure of which is incorporated by reference. Specific methods for making such dyes are well known in the art and can be found, for example, in U.S. Pat. Nos. 5,795,981; 5,656,750; 5,492,795; 4,677,045; 5,237,498; and 5,354,873, the disclosures of each of which are incorporated by reference. In some embodiments, such dyes will contain functional groups capable of forming a stable fluorescent product with functional groups typically found in biomolecules or polymers including activated esters, isothiocyanates, amines, hydrazines, halides, acids, azides, maleimides, alcohols, acrylamides, haloacetamides, phenols, thiols, acids, aldehydes and ketones.

In some embodiments, in addition to specific squaric acid dyes, other dyes can be further selected for use as identifiers for the polymeric beads from cyclobutenedione derivatives, substituted cephalosporin compounds, fluorinated squaraine compositions, symmetrical and unsymmetrical squaraines, alkylalkoxy squaraines, or squarylium compounds. Some of these dyes can fluoresce at near infrared as well as at infrared wavelengths that would effectively expand the range of emission spectra up to about 1,000 nm.

In further embodiments, hydrophobic dyes, such as phtalocyanines and naphfhalocyanines, can also be selected as operating at longer wavelengths. Other classes of fluorochromes are equally suitable for use as dyes as identifiers for the beads (such as, polymeric beads) in present invention. Non-limiting examples of these dyes include: 3-Hydroxypyrene 5,8,10-Tri Sulfonic acid, 5-Hydroxy Tryptamine, 5-Hydroxy Tryptamine (5-HT), Acid Fuhsin, Acridine Orange, Acridine Red, Acridine Yellow, Acriflavin, AFA (Acriflavin Feulgen SITSA), Alizarin Complexon, Alizarin Red, Allophycocyanin, ACMA, Aminoactinomycin D, Aminocoumarin, Anthroyl Stearate, Aryl- or Heteroarylsubstituted Polyolefin, Astrazon Brilliant Red 4G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF, Berberine Sulphate, Bisbenzamide, BOBO 1, Blancophor FFG Solution, Blancophor SV, Bodipy Fl, BOPRO 1 Brilliant Sulphoflavin FF, Calcien Blue, Calcium Green, Calcofluor RW Solution, Calcofluor White, Calcophor White ABT Solution, Calcophor White Standard Solution, Carbocyanine, Carbostyryl, Cascade Blue, Cascade Yellow, Catecholamine, Chinacrine, Coriphosphine O, Coumarin, Coumarin-Phalloidin, CY3.1 8, CY5.1 8, CY7, Dans (1-Dimethyl Amino Naphaline 5 Sulphonic Acid), Dansa (Diamino Naphtyl Sulphonic Acid), Dansyl NH—CH3, DAPI, Diamino Phenyl Oxydiazole (DAO), Dimethylamino-5-Sulphonic acid, Dipyrrometheneboron Difluoride, Diphenyl Brilliant Flavine 7GFF, Dopamine, Eosin, Erythrosin ITC, Ethidium Bromide, Euchrysin, FIF (Formaldehyde Induced Fluorescence), Flazo Orange, Fluo 3, Fluorescamine, Fura-2, Genacryl Brilliant Red B, Genacryl Brilliant Yellow 10OGF, Genacryl Pink 3G, Genacryl Yellow SGF, Gloxalic Acid, Granular Blue, Haematoporphyrin, Hoechst 33258 (bound to DNA), Indo-1, Intrawhite Cf Liquid, Leucophor PAF, Leucophor SF, Leucophor WS, Lissamine Rhodamine B200 (RD200), Lucifer Yellow CH, Lucifer Yellow VS, Magdala Red, Marina Blue, Maxilon Brilliant Flavin 10 GFF, Maxilon Brilliant Flavin 8 GFF, MPS (Methyl Green Pyronine Stilbene), Mithramycin, NBD Amine, Nile Red, Nitrobenzoxadidole, Noradrenaline, Nuclear Fast Red, Nuclear Yellow, Nylosan Brilliant Flavin EBG, Oregon Green, Oxazine, Oxazole, Oxadiazole, Pacific Blue, Pararosaniline (Feulgen), Phorwite AR Solution, Phorwite BKL, Phorwite Rev, Phorwite RPA, Phosphine 3R, Phthalocyanine, Phycoerythrin R, Polyazaindacene Pontochrome Blue Black, Porphyrin, Primuline, Procion Yellow, Propidium Iodide, Pyronine, Pyronine B, Pyrozal Brilliant Flavin 7GF, Quinacrine Mustard, Rhodamine 123, Rhodamine 5 GLD, Rhodamine 6G, Rhodamine B, Rhodamine B 200, Rhodamine B Extra, Rhodamine BB, Rhodamine BG, Rhodamine WT, Rose Bengal, Serotonin, Sevron Brilliant Red 2B, Sevron Brilliant Red 4G, Sevron Brilliant Red B, Sevron Orange, Sevron Yellow L, SITS (Primuline), SITS (Stilbene Isothiosulphonic acid), Stilbene, Snarf 1, sulphO Rhodamine B Can C, Sulpho Rhodamine G Extra, Tetracycline, Texas Red, Thiazine Red R, Thioflavin S, Thioflavin TCN, Thioflavin 5, Thiolyte, Thiozol Orange, Tinopol CBS, TOTO 1, TOTO 3, True Blue, Ultralite, Uranine B, Uvitex SFC, Xylene Orange, XRITC, YO PRO 1, or combinations thereof. Selection of the appropriate dye will vary, depending on the specific desired emission of light from the dye as well as the dye's hydrophobicity.

The spectral properties of the fluorescent dyes should be sufficiently similar in excitation wavelengths and intensity to fluorescein or rhodamine derivatives as to permit the use of the same flow cytometry or microscopy equipment. It is preferable that the dyes, however, have higher solubility in organic solvents and have improved photostability and quantum yields. These dyes will be combined at predetermined ratio and embedded into a polymeric bead vehicle and total dye quantity will be between about 0.00001% and 15%, such as by about 0.0001% and 15%, 0.001% and 15%, 0.01% and 15%, 0% and 15%. 1% and 15%, 1% and 15%, 2% and 15%, 3% and 15%, 4% and 15%, 5% and 15%, 6% and 15%, 7% and 15%, 8% and 15%, 9% and 15%, 10% and 15%, 11% and 15%, 12% and 15%, 13% and 15%, 14% and 15%, by weight to the weight of the polymeric bead.

F. Radio Frequency Coded Beads

In some aspects, the identifier associated with any of the polymeric bead compositions described herein is a radio frequency identification (RFID) signal. In some embodiments, embedded within the core of the bead compositions described herein is an RFID chip. The radio frequency associated with each bead (such as, a polymeric bead) can be decoded by an imaging processor to identify a capture agent that is bound to the surface of a particular polymeric bead in the plurality of polymeric beads. In other embodiments, the radio frequency associated with a polymeric bead in the plurality of polymeric beads can be decoded by an imaging processor (such as an imaging processor that includes an RFID chip reader as a component) to identify other sources of information not strictly related to assay being conducted per se. These can include, but are not limited to, the identity of the assay, the manufacturing lot of the plurality of polymeric beads, or a locational identifier (such as, but not limited to, the location of a hospital, a doctor's office, or a laboratory). In another embodiment, further radio frequencies associated with a polymeric bead in the plurality of polymeric beads can be pre-labeled for calibration of the imaging processor. In other embodiments, the radio frequency associated with a bead in a plurality of beads can be decoded by an imaging processor to identify more than one piece of information, such as more than one piece of information of the types above.

In some aspects, the RFID chips can be small enough to be completely embedded within the cores of the beads (such as, polymeric beads) of some of the compositions described herein. In some embodiments, the RFID chip can be smaller than about 1 mm×1 mm×1 mm in size. In other embodiments, the chips can be smaller than about 0.5 mm×0.5 mm×0.5 mm in size. In other embodiments, the chips can be about 0.4 mm×0.4 mm×0.4 mm in size. In some embodiments, the RFID chip can measure less than about 100 $\mu m \times 100 \ \mu m \times 50 \ \mu m$ in size. In other embodiments, the RFID chip can measure less than about 50 $\mu m \times 50 \ \mu m \times 25 \ \mu m$ in size. In another embodiment, the RFID chip can measure less than about 50 $\mu m \times 50 \ \mu m \times 10 \ \mu m$ in size. In other embodiments, the RFID chip can measure less than about 45 $\mu m \times 45 \ \mu m \times 5 \ \mu m$, less than about 40 $\mu m \times 40 \ \mu m \times 5 \ \mu m$, less than about 35 $\mu m \times 35 \ \mu m \times 5 \ \mu m$, less than about 30 $\mu m \times 30 \ \mu m \times 5 \ \mu m$, less than about 25 $\mu m \times 25 \ \mu m \times 5 \ \mu m$, less than about 20 $\mu m \times 20 \ \mu m \times 5 \ \mu m$, less than about 15 $\mu m \times 15 \ \mu m \times 5 \ \mu m$, less than about 10 $\mu m \times 10 \ \mu m \times 5 \ \mu m$, or less than about 5 $\mu m \times 5 \ \mu m \times 5 \ \mu m$, inclusive, including any other dimension in between these numbers. In still another embodiment, the RFID chip can measure less than about 50 $\mu m \times 50 \ \mu m \times 5 \ \mu m$ in size. In some embodiments, the volume of the RFID chip can be less than about 62,500 $\mu m^3$. In other embodiments, the volume of the RFID chip can be between about 50,000 and 60,000 $\mu m^3$, between about 40,000 and 50,000 $\mu m^3$, between about 30,000 and 40,000 $\mu m^3$, between about 20,000 and 30,000 $\mu m^3$, or between about 10,000 and 20,000 $\mu m^3$, inclusive. In other embodiments, the volume of the RFID chip can be about 10,125 $\mu m^3$, about 8000 $\mu m^3$, about 6125 $\mu m^3$, about 4500 $\mu m^3$, about 3125 $\mu m^3$, about 2000 $\mu m^3$, about 1125 $\mu m^3$, about 500 $\mu m^3$, or about 125 $\mu m^3$, inclusive, as well as any volume in between these numbers. In another embodiment, the volume of the RFID chip can be about 12,500 $\mu m^3$.

The RFID chip completely embedded within the polymeric beads of some of the compositions described herein can be passive (i.e. requiring no internal power source, a passive chip uses the energy from an electromagnetic wave sent by an RFID chip reader to transmit a radio signal), active (i.e. containing a battery or some other power source that always broadcasts or beacons its signal), or semi-active (i.e. having a small power source activated when in the presence of an RFID reader), In some aspects, the RFID chip can have an integrated circuit and an internal antenna. The antenna can be made out of any suitable material conducive for the transmission of radio waves. In some embodiments, the antenna can be made of a nonfunctional ferromagnetic or paramagnetic material capable of attraction in a magnetic field.

In other aspects, the RFID chip can be an optical RFID chip with photovoltaic components and an integrated circuit. Unlike other RFID chips, which use radio frequencies to induce transmission in passive chips, optical RFID chips operate in the electromagnetic spectrum between the frequencies of 333 THz ($3.33 \times 10^{14}$ Hz, 900 nm), 380 THz (788 nm), and 750 THz (400 nm). In some embodiments, the optical RFID chip can have a light emitting diode (LED) on an integrated circuit. In other embodiments, the LED can be an infrared LED (IR LED), an ultraviolet LED (UV LED), or a visible light LED. The photovoltaic components of the optical RFID chip are used to provide energy for the chip to transmit a radio wave in response to concentrated light. In some embodiments, the concentrated light can be in the visible spectrum. In other embodiments, the concentrated light can be in the IR spectrum. In other embodiments, the concentrated light can be in the UV spectrum. In another embodiment, the concentrated light can be provided by a laser. In some embodiments, the optical RFID chips may not require an antenna for transmission of a radio signal. In other embodiments, optical RFID chips can contain a nonfunctional ferromagnetic or paramagnetic material capable of attraction in a magnetic field.

The RFID chips contemplated for use in the compositions described herein can operate at a frequency in the range of 30 MHz to 30 GHz, inclusive, as well as any frequency in between. In some aspects, the RFID chips can operate in frequencies in the High Frequency (HF), Very High Frequency (VHF), Ultra High Frequency (UHF), or the Super High Frequency (SHF) bands of the radio spectrum. In some embodiments, the RFID chips can operate at a frequency of between about 30-100 MHz, between about 100-200 MHz, between about 300-400 MHz, between about 400-500 MHz, between about 500-600 MHz, between about 600-700 MHz, between about 700-800 MHz, between about 800-900 MHz, between about 900 MHz to 1 GHz, between about 1-1.1 GHz, between about 1.1-1.2 GHz, between about 1.2-1.3 GHz, between about 1.3-1.4 GHz, between about 1.4-1.5 GHz, between about 1.5-1.6 GHz, between about 1.6-1.7 GHz, between about 1.7-1.8 GHz, between about 1.8-1.9 GHz, between about 2.0-2.1 GHz, between about 2.1-2.2 GHz, between about 2.2-2.3 GHz, between about 2.3-2.4 GHz, between about 2.4-2.5 GHz, between about 2.5-2.6 GHz, between about 2.6-2.7 GHz, between about 2.7-2.8 GHz, between about 2.8-2.9 GHz, between about 2.9-3.0 GHz, between about 3.0-5.0 GHz, between about 5-10 GHz, between about 10-15 GHz, between about 15-20 GHz, between about 20-25 GHz, or between about 25-30 GHz, inclusive. In some embodiments, the RFID chips can operate at a frequency of about 2.45 GHz. In other embodiments, the RFID chips can operate at a frequency of between about 860-960 MHz, inclusive, including any frequency in between. The RFID chips can transmit radio waves over a distance of about 300 mm or less. In some embodiments, the RFID chips can transmit radio waves over a distance of between about 200-300 mm or about 100-200 mm, inclusive. In other embodiments, the RFID chips can transmit radio waves over a distance of about 90 mm, about 80 mm, about 70 mm, about 60 mm, about 50 mm, about 40 mm, about 35 mm, about 30 mm, about 25 mm, about 20 mm, about 15 mm, about 14 mm, about 13 mm, about 12 mm, about 11 mm, about 10 mm, about 9 mm, about 8 mm, about 7 mm, about 6 mm, about 5 mm, about 4 mm, about 3 mm, about 2 mm, about 1 mm, 0.9 mm, 0.8 mm, 0.7 mm, 0.6 mm, 0.5 mm, 0.4 mm, 0.2 mm, or 0.1 mm, inclusive, including any value between these numbers. In some embodiments, the RFID chips can transmit radio waves over a distance of between about 0.5 mm to about 1 mm.

In some aspects, each RFID chip in the compositions described herein can transmit radio waves over short periods of time. Shorter transmission times reduce the amount of energy required for passive or semi-active RFID chip radio wave transmission and also permits faster detection of the radio wave transmissions from each member of a plurality of bead-embedded RFID chips by an RFID chip reader. In some embodiments, the RFID chips of the compositions described herein can transmit radio waves for less than about 500 milliseconds. In other embodiments, the RFID chips of the compositions described herein can transmit radio waves for between about 400-500 milliseconds, between about 300-400 milliseconds, between about 200-300 milliseconds, between about 100-200 milliseconds, between about 50-100 milliseconds, between about 45-50 milliseconds, 40-45 milliseconds, 35-40 milliseconds, 30-35 milliseconds, or 25-30 milliseconds, inclusive. In another embodiment, the RFID chips of the compositions described herein can transmit radio waves for about 24 milliseconds, about 23 milliseconds, about 22 milliseconds, about 21 milliseconds, about 20 milliseconds, about 19 milliseconds, about 18 milliseconds, about 17 milliseconds, about 16 milliseconds, about 15 milliseconds, about 14 milliseconds, about 13 milliseconds, about 12 milliseconds, about 11 milliseconds, about 10 milliseconds, about 9 milliseconds, about 8 milliseconds, about 7 milliseconds, about 6 milliseconds, about 5 milliseconds, about 4 milliseconds, about 3 milliseconds, about 2 milliseconds, or about 1 millisecond, inclusive, as well as any value in between these numbers.

The RFID chip completely embedded within the polymeric beads of the compositions described herein can have a non-volatile memory which can include, but not limit to, a read only memory (ROM), an erase-able read only memory (EROM), or a flash memory for storage of a unique radio frequency identification code. It is this identification code that permits the identity of any individual bead (such as, a polymeric bead) of the compositions described herein to be readily ascertained by an RFID chip reader, which can be a component of an imaging processor. In some embodiments, the individual identification code can be based on an identification number of any of 16, 32, 64, or 128 bits. In some embodiments, the individual identification code can be a 3, 4, 5, 6, 7, 8, 9, 10, 11, 12, or 13 digit number. In other embodiments, the individual identification code can be a 14, 15, 16, 17, 18, 19, 20, 21, 22, 23, 24, 25, 26, 27, 28, 29, 30, 31, 32, 33, 34, 35, 36, 37, or 38 digit number. Suitable RFID chips can be, for example, RFID "powder" chips supplied by Hitachi (See, e.g., www.hitachi.com/New/cnews/070213c.pdf), the RFID "mu-chip" from Hitachi (www.hitachi.co.jp/Prod/mu-chip; See also U.S. Pat. No. 7,592,914), ELAMS™ chips from Biomedic Data Systems (www.bmds.com/products/transponders), UCODE G2 XM OCA chips from SEC International (www.fecinc.com.my/otherproducts/epc_oca.htm), and TIRIS™ chips from Texas Instruments (www.ti.com/rfid/).

The RFID chips described herein are each completely embedded within a polymeric material to form a polymeric bead of a particular shape. Any polymeric material capable of forming a polymeric bead and completely embedding an RFID chip can be used for the polymeric beads of the compositions described herein. RFID integrated circuit chips are typically encapsulated by a polymeric material such as an organic resin (e.g. an epoxy resin) or other suitable material during the standard RFID chip fabrication process. The encapsulating material (sometimes referred to as "glob-top") is later cured into a hard protective coating that protects the integrated circuit chip from environmental conditions such as humidity and moisture. (See, e.g. U.S. Pat. No. 7,884,719; U.S. Patent Application Publication Nos: 2006/0205115 and 2008/0129455, the contents of which are hereby incorporated by reference herein in their entirety).

Most of the same polymeric materials used for encapsulating and protecting the RFID chip integrated circuit can also be used for making the polymeric beads of the compositions described herein. In some aspects the polymeric material used to construct the polymeric beads of the present invention is a composite of an organic resin (e.g. an epoxy resin), phenolic hardeners, and other chemicals. These polymeric materials are readily available and well known in the art. See, for example, Warad, *IC Packaging: Package Construction Analysis in Ultra Small IC Packaging*, LAP LAMBERT Academic Publishing (2010); *The Electronic Packaging Handbook*, CRC Press (Blackwell, ed.), (2000); Pecht et al., *Electronic Packaging Materials and Their Properties*, CCR Press, $1^{st}$ ed., (1998), the contents of each of which are incorporated herein by reference in their entirety. These types of hydrophobic organic resin materials have the advantage of not swelling in aqueous environments which ensures that uniform polymeric bead size and shape are maintained within the population of polymeric beads. Suitable polymeric resins for fabrication of the compositions described herein include, but are not limited to, the EPON™ family of epoxy resins provided by Hexion Specialty Chemicals, Inc. (Columbus, Ohio) and any number of epoxy resins provided by The Dow Chemical Company (Midland, Mich.). In one embodiment, the polymeric material used to fabricate the polymeric beads can be SU-8 2010 epoxy-based negative photoresist polymer. In some embodiments, the polymeric material for encapsulating an RFID chip can be opaque or transparent, such that it permits visible light to reach an optical RFID chip embedded within a polymeric bead.

G. Capture Agents

In some aspects, the beads of the compositions described herein can be attached to a unique capture agent. By "unique capture agent," it is meant that each capture agent is associated with a specific bead having a particular identifier. The capture agent can be any biomolecule or a chemical compound capable of binding one or more biomolecules or chemical compounds present in the solution. Examples of biomolecule capture agents include, but are not limited to, a DNA molecule, a DNA-analog-molecule, an RNA-molecule, an RNA-analog-molecule, an amino-acid, a nucleotide, a protein, an enzyme, a lipid, a phospholipid, a carbohydrate moiety, a polysaccharide, an antigen, a virus, a cell, an antibody, or an antibody fragment. Examples of chemical compound capture agents include, but are not limited to, individual components of chemical libraries, small molecules, or environmental toxins (for example, pesticides or heavy metals). In some embodiments, the capture agent can be chemically attached the bead (such as, a polymeric bead). In other embodiments, the capture agent can be physically absorbed to the surface of the bead. In some embodiments, the attachment linkage between the capture agent and the bead can be a covalent bond. In other embodiments, the attachment linkage between the capture agent and the bead can be a non-covalent bond including, but not limited to, a salt bridge or other ionic bond, one or more hydrogen bonds, hydrophobic interactions, van der Waals force, London dispersion force, a mechanical bond, one or more halogen bonds, aurophilicity, intercalation, or stacking.

In one aspect, the binding of an analyte (such as a signal-emitting entity-labeled chemical compound or biomolecule) to a capture agent-bound bead can be detected by any apparatus capable of detecting the presence of the signal-emitting entity (for example, an imagining processor). In some embodiments, flow cytometry can be used to detect the presence of the signal-emitting entity. Flow cytometry uses the principles of light scattering, light excitation, and emission from fluorochrome reporter molecules and can be used to generate specific multi-parameter data from beads bound to reporter-labeled chemical compounds or biomolecules. Bead compositions (such as those described herein) can be hydro-dynamically focused in a sheath of a buffer solution before intercepting an optimally focused light source. In some embodiments, a laser can be used as a light source in flow cytometry. In some embodiments, the imaging processor can comprise both a flow cytometry instrument and an RFID chip reader, both to identify the capture agent bound to the uniquely identifiable bead and to measure the signal from a signal-emitting entity-labeled chemical compound or biomolecule bound to the capture agent, simultaneously. In other embodiments, the identity of the bead (such as, a polymeric bead) bound to the capture agent as supplied by the RFID chip reader and the measurement of the signal from the signal-emitting entity-labeled chemical compound or biomolecule bound to the capture agent as supplied by the flow cytometry apparatus can both be displayed in a machine readable format. In other embodiments, the imaging processor can comprise both a flow cytometry instrument and a code detector (for example, a light scanner or a CCD sensor) for decoding the encoded pattern (such as a barcode) associated with a bead, both to identify the capture agent bound to the uniquely identifiable bead and to measure the signal from a signal-emitting entity-labeled chemical compound or biomolecule bound to the capture agent, simultaneously.

In some aspects, the bead compositions described herein can be used to detect the presence of a particular chemical compound or biomolecule in the solution. Accordingly, in some embodiments, the binding of the capture agent to a chemical compound or biomolecule in the solution can indicate the presence of the chemical compound or biomolecule in the solution.

In some aspects, the bead compositions described herein can be used to detect the concentration of a particular chemical compound or biomolecule in the solution. Accordingly, in some embodiments, the binding of the capture agent to a chemical compound or biomolecule in the solution indicates the concentration of the chemical compound or biomolecule in the solution.

In some aspects, the bead compositions described herein can be used to determine the binding affinity of the capture agent for a particular chemical compound or biomolecule in the solution. Accordingly, in some embodiments, the binding of the capture agent to a chemical compound or biomolecule in the solution indicates the binding affinity of the capture agent for a particular chemical compound or biomolecule in the solution.

H. Signal-Emitting Entities

In some aspects, analytes in a sample (such as a biological sample) that are capable of binding to a capture agent are labeled with a signal-emitting entity capable of emitting a detectable signal upon binding to the capture agent. In some embodiments, the signal-emitting entity can be colorimetric based. In other embodiments, the signal-emitting entity can be fluorescence-based including, but not limited to, phycoerythrin, blue fluorescent protein, green fluorescent protein, yellow fluorescent protein, cyan fluorescent protein, and derivatives thereof. In other embodiments, the signal-emitting entity can be radioisotope based, including, but not limited to, molecules labeled with $^{32}$P, $^{33}$P, $^{22}$Na, $^{36}$Cl, $^{2}$H, $^{3}$H, $^{35}$S, and $^{123}$I. In other embodiments, the signal-emitting entity is light-based including, but not limited to, luciferase (e.g. chemiluminescence-based) horseradish peroxidase, alkaline phosphatase, and derivatives thereof. In some embodiments, the biomolecules or chemical compounds present in the sample can be labeled with the signal-emitting entity prior to contact with a bead (such as, polymeric bead) composition. In other embodiments, the biomolecules or chemical compounds present in the sample can be labeled with the signal-emitting entity subsequent to contact with a bead composition.

IV. Methods of the Invention

Provided herein are methods using the bead (such as, polymeric bead) compositions provided herein for conducting biological or chemical multiplex assays.

A. Attachment of Capture Agents to Bead Surfaces

In some aspects, the methods for producing the plurality of bead compositions described herein can further include attaching a capture agent (such as, but not limited to, a chemical compound or biomolecule) to the surface of the beads. The epoxy groups on the surface of fabricated beads can be modified to facilitate attachment to various chemical compounds or biomolecules. Suitable biomolecules for attachment to the beads include, but are not limited to, a DNA molecule, a DNA-analog-molecule, an RNA-molecule, an RNA-analog-molecule, an amino-acid, a nucleotide, a protein, an enzyme, a lipid, a phospholipid, a carbohydrate moiety, a polysaccharide, an antigen, a virus, a cell, an antibody, a small molecule chemical compound, or an antibody fragment. Furthermore, any suitable chemical compound can be attached to the surface of the beads including, for example, individual components of multi-member chemical libraries. In other embodiments, one or more biomolecules or chemical compounds can be physically absorbed to the surface of the bead. In some embodiments, the attachment linkage between the chemical compound or biomolecule and the bead (such as, a polymeric bead) can be a covalent bond. In other embodiments, the attachment linkage between the chemical compound or biomolecule and the bead can be a non-covalent bond including, but not limited to, a salt bridge or other ionic bond, one or more hydrogen bonds, hydrophobic interactions, van der Waals force, London dispersion force, a mechanical bond, one or more halogen bonds, aurophilicity, intercalation, or stacking.

In one non-limiting embodiment, a carbonyl group can be introduced onto the surface of an epoxy polymeric bead by reacting with amino acids such as beta-alanine. These carboxyl functionalities can then be used to form covalent bonds with amino groups of any chemical compound or biomolecule. In another non-limiting embodiment, the epoxy groups on the surface of the beads can be treated with cystamine followed by reduction using dithiothreonine (DTT). This results in free thiol becoming available to form disulfide bonds with sulfhydral groups of any chemical compound or biomolecule. In another non-limiting embodiment, the polymer surface can be decorated with free amines by reacting the epoxy polymer with excess ethylenediamine. The resulting free amino groups will attach to chemical compounds or biomolecules via carboxyl groups. In yet another non-limiting embodiment, the epoxide on the surface can be hydrolyzed to form hydroxyl groups. These high density hydroxyl groups can then be silanized with various siloxanes. Silanization has been widely used in the chemical industry to create vast different kinds of surfaces, and there are many types of silanxones available commercially and known in the art. Silanization can therefore be used to create many different surfaces for attachment of chemical compounds or biomolecules to the surface of the bead compositions described herein. In some embodiments, large biomolecules, such as proteins can be attached to the beads by physical absorption due to formation of one or more non-covalent bonds including, but not limited to, one or more salt bridge or other ionic bond, one or more hydrogen bonds, hydrophobic interactions, van der Waals force, London dispersion force, a mechanical bond, one or more halogen bonds, aurophilicity, intercalation, or stacking between proteins and the surface properties of the beads. The attachment by physical absorption does not require any chemical reaction and is often used, for example, in the preparation of solid phase for immunoassays.

A combinatorial chemical library is a collection of multiple species of chemical compounds comprised of smaller subunits or monomers. Combinatorial libraries come in a variety of sizes, ranging from a few hundred to many hundreds of thousand different species of chemical compounds. There are also a variety of library types, including oligomeric and polymeric libraries comprised of compounds such as peptides, carbohydrates, oligonucleotides, and small organic molecules, etc. Such libraries have a variety of uses, such as immobilization and chromatographic separation of chemical compounds, as well as uses for identifying and characterizing ligands capable of binding an acceptor molecule or mediating a biological activity of interest.

Various techniques for synthesizing libraries of compounds on solid-phase supports are known in the art. Solid-phase supports are typically polymeric objects with surfaces that are functionalized to bind with subunits or monomers to form the compounds of the library. Synthesis of one library typically involves a large number of solid-phase supports.

To make a combinatorial library, solid-phase supports are reacted with one or more subunits of the compounds and with one or more numbers of reagents in a carefully controlled, predetermined sequence of chemical reactions. In other words, the library subunits are "grown" on the solid-phase supports. The larger the library, the greater the number of reactions required, complicating the task of keeping track of the chemical composition of the multiple species of compounds that make up the library. Thus, it is important to have methods and apparatuses which facilitate the efficient production of large numbers of chemical compounds, yet allow convenient tracking of the compounds over a number of reaction steps necessary to make the compounds.

The beads (such as, polymeric beads) of the compositions of the invention are applicable to any type of chemical reaction that can be carried out on a solid support. Such chemical reactions include, but are not limited to, 2+2 cycloadditions including trapping of butadiene; [2+3]cycloadditions including synthesis of isoxazolines, furans and modified peptides; acetal formation including immobilization of diols, aldehydes and ketones; aldol condensation including derivatization of aldehydes, synthesis of propanediols; benzoin condensation including derivatization of aldehydes; cyclocondensations including benzodiazepines and hydantoins, thiazolidines, turn mimetics, porphyrins, phthalocyanines; Dieckmann cyclization including cyclization of diesters; Diels-Alder reaction including derivatization of acrylic acid; Electrophilic addition including addition of alcohols to alkenes; Grignard reaction including derivatization of aldehydes; Heck reaction including synthesis of disubstituted alkenes; Henry reaction including synthesis of nitrile oxides in situ (see 2+3 cycloaddition); catalytic hydrogenation including synthesis of pheromones and peptides (hydrogenation of alkenes); Michael reaction including synthesis of sulfanyl ketones, bicyclo[2.2.2]octanes; Mitsunobu reaction including synthesis of aryl ethers, peptidyl phosphonates and thioethers; nucleophilic aromatic substitutions including synthesis of quinolones; oxidation including synthesis of aldehydes and ketones; Pausen-Khand cycloaddition including cyclization of norbornadiene with pentynol; photochemical cyclization including synthesis of helicenes; reactions with organo-metallic compounds including derivatization of aldehydes and acyl chlorides; reduction with complex hydrides and tin compounds including reduction of carbonyl, carboxylic acids, esters and nitro groups; Soai reaction including reduction of carboxyl groups; Stille reactions including synthesis of biphenyl derivatives; Stork reaction including synthesis of substituted cyclohexanones; reductive amination including synthesis of quinolones; Suzuki reaction including synthesis of phenylacetic acid derivatives; and Wittig-Horner reactions including reactions of aldehydes, pheromones, and sulfanyl ketones.

References disclosing the synthesis of chemical libraries as well as the deconvolution of the individual compounds of those libraries onto individual solid phase supports (e.g., polymeric bead compositions such as those disclosed herein), can be found in U.S. Patent Application No. 2009/0032592; Needels et al., (1993), *Proc. Natl. Acad. Sci. USA* 90: 10700-10704; International Patent Application Publication No: WO 97/15390, the disclosures of each of which are incorporated by reference herein in their entireties.

B. Methods for Identifying One Bead Out of a Plurality of Beads

Provided herein are methods for identifying a single bead from the plurality of bead compositions described herein. When using the bead compositions described herein for multiplex screening assays, individual beads attached to a capture agent (e.g. a known chemical compound (such as an individual member of a combinatorial chemical library) or a known biomolecule) can be identified by virtue of the unique identifier associated with each bead in the composition. In other embodiments, an identifier associated with at least one bead in a plurality of beads (such as, polymeric beads) can be decoded by an imaging processor to identify other sources of information not strictly related to assay being conducted per se. These can include, but are not limited to, the identity of the assay, the manufacturing lot of the plurality of beads, or a locational identifier. In another embodiment, further identifiers associated with a bead in the plurality of beads can be pre-labeled for calibration of the imaging processor. In other embodiments, the identifier associated with a bead in a plurality of beads can be decoded by an imaging processor to identify more than one type of information, such as those described above.

Accordingly, in one aspect, a single bead can be identified by injecting a composition comprising a plurality of beads into a conduit comprising a width of less than twice the width of an individual bead, wherein each bead in the composition is of substantially identical size and shape, and comprises at least one (such as, at least one, two, three, or four) unique identifiers followed by the step of identifying the identifier. In one embodiment, the identifier is an encoded pattern or a combination of encoded patterns (such as a barcode) and is identified by decoding the encoded pattern or a combination of encoded patterns on the surface of the bead by an imaging processor. In another embodiment, the identifier is a fluorescent dye with a particular wavelength and is identified by detecting the light emitted by the dye by an imaging processor. In yet another embodiment, the identifier is an RFID signal and is identified by emitting an electromagnetic wave from an RFID chip reader, which can be a component of an imaging processor, to cause transmission of a radio wave comprising a unique identifier from the RFID chip embedded in an individual polymeric bead; receiving the radio wave by the RFID reader; and identifying the unique identification code from the individual bead based on the radio wave transmission.

1. Conduits

In some aspects, the methods described herein can utilize a conduit for individually guiding or funneling a composition of a plurality of beads, such as those described herein, to an imaging processor. The conduit can be constructed in such a way as to permit only one bead (such as, a polymeric bead) to interact with the imaging processor at any one time. In one embodiment, the conduit can have (i) large openings at a first end and (ii) small openings at a second end. In another embodiment, the conduit can have a width of less than twice the width of an individual polymeric bead at its widest dimension. In some embodiments, the conduit can have a first end large enough to permit injection of a plurality of beads, such as those described herein, into the conduit. In some embodiments, the first end large enough to permit injection of a plurality of beads is located at an elevation lower than the second end, causing the plurality of bead composition to flow upwards against the force of gravity.

The transverse shape of the conduit can be any shape sufficient to accommodate the shape of the plurality of beads of substantially identical size and shape, such as the compositions described herein, that are injected into the conduit. Accordingly, the transverse shape of the conduit can be, without limitation, square, circular, rectangular, triangular, ovoid, or any other shape sufficiently identical to the beads described herein.

The conduit can be made of any suitable material including, but not limited to, steel, non-ferrous metals (e.g. aluminum, copper, tin and alloys thereof), plastic material (e.g., PE, PP, PVC, ABS), or plastic (GRP), or other materials such as, glass, fiber cement, or ceramic.

The conduit can be located near an imaging processor, to allow the imaging processor to identify the one or more identifiers associated with a bead (such as, a polymeric bead) passing near the imaging processor. In some embodiments, the conduit can be located about 300 mm or less from the imaging processor. In some embodiments, the conduit can be located between about 200-300 mm or about 100-200 mm, inclusive from the imaging processor. In other embodiments, the conduit can be located about 90 mm, about 80 mm, about 70 mm, about 60 mm, about 50 mm, about 40 mm, about 35 mm, about 30 mm, about 25 mm, about 20 mm, about 15 mm, about 14 mm, about 13 mm, about 12 mm, about 11 mm, about 10 mm, about 9 mm, about 8 mm, about 7 mm, about 6 mm, about 5 mm, about 4 mm, about 3 mm, about 2 mm, about 1 mm, 0.9 mm, 0.8 mm, 0.7 mm, 0.6 mm, 0.5 mm, 0.4 mm, 0.2 mm, or 0.1 mm, inclusive, including any value between these numbers, from the imaging processor. In another embodiment, the conduit can be located about 0.5 mm to about 1 mm from the imaging processor.

2. Encoded Pattern Readers a. Microfluidic-Based Imaging Processors

In another aspect of the present invention, a microfluidic apparatus can be used in conjunction with an imaging processor to decode an encoded pattern or a combination of encoded patterns (such as a barcode) associated with a bead (such as any of the beads disclosed herein). The microfluidic apparatus comprises a conduit, such as a micro flow channel, sized and configured to guide coded beads to advance one at a time pass a decoding zone associated with the imaging processor. The decoding zone includes a code detector (such as a light scanner, a CCD sensor, etc.) that detects the pattern of transmitted light through each coded bead for decoding the code represented by the image thereon. The conduit of the microfluidic apparatus has an internal cross section that has a geometry that is sized and shaped to receive and allow the coded bead to pass through when a particular cross section of the coded bead is aligned with the cross section of the conduit, thereby presenting the coded bead in a particular orientation with respect to the decoding zone. In one embodiment, the geometry of the internal cross section of the conduit is sized and shaped to receive and allow the coded bead (such as, a polymeric bead) to pass through when the smallest cross section of the coded bead is aligned with the conduit (e.g., the long axis of the coded bead is aligned with the axis of the conduit). The microfluidic apparatus can include more than one conduit, to provide decoding of coded beads in parallel channels.

A decoding system associated with the imaging processor, positioned with respect to the decoding zone, includes a light source and an optical sensor. In one embodiment, the light source can be a diode laser at any of 200 nm, 250 nm, 300 nm, 350 nm, 400 nm, 450 nm, 500 nm, 550 nm, 600 nm, 650 nm, 700 nm, 750 nm, 800 nm, 850 nm, or 900 nm wavelengths, inclusive, including wavelengths in between these values. In another embodiment, the decoding system has an objective lens (such as a 5×, 10×, 15×, 20×, 25×, 30×, 35×, 40×, 45×, 50×, 55×, 60×, 65×, 70×, 75×, 80×, 85×, 90×, 95×, or 100× objective lens, inclusive, including any number in between these values). In another embodiment, the optical sensor can be a high-speed photon detector and include digital readout electronics. Alternatively, an area light source (e.g., a laser beam having a large enough spot size) can be used to project light to simultaneously cover the entire area of the coded pattern on the bead, and an area optical sensor such as a CCD sensor can be used to image simultaneously the entire coded pattern and the light transmitted there through. Alternatively, a line scan camera can be used for the optical sensor.

As the beads pass through the decoding zone associated with the imaging processor, light from the laser is transmitted through and the light intensity is detected, by the photon detector and directly converted into 1's and 0's using threshold detection. The position of the slits on the bead determines which of the bits is the least significant bit (LSB) and the most significant bit (MSB). In some embodiments, a slight orientation variation of the bead in the confined conduit does not significantly affect the efficiency of the optical detection and subsequent decoding.

In a further embodiment, the imaging processor can also comprise a reaction detection system (e.g., a fluorescence detector, an absorption detector, or a chemiluminescence detector) for detecting the result of reactions that have taken place between an analyte in a sample and the capture agent immobilized to the surface of the bead (such as, a polymeric bead). In some embodiments, a signal-emitting entity can be used for detection of a positive or negative reaction between an analyte and the capture agent and the signal emitted from the signal emitting entity detected by the reaction detection system. The signal-emitting entity can be, without limitation, a fluorescence label, chemiluminescence label or other light-emitting label, an absorption label, or a radioactive label. Thus, for example, in configurations employing fluorescent signal-emitting entities, the reaction detection system can include a light source that produces light at an appropriate wavelength for activating the fluorescent material, as well as optics for directing the light source through an optically clear detection window for observing material in the sample cell. The light source can be any number of light sources that provide one or more appropriate wavelengths, including, e.g., lasers, laser diodes, and LEDs. Other light sources can be used in other detection systems. For example, broad band light sources can be employed in light scattering/transmissivity detection schemes, and the like.

In some aspects, the beads of any of the compositions described herein can be magnetic. In one embodiment, an electromagnet can be used to temporarily immobilize the polymeric bead for decoding of one or more encoded patterns (such as a barcode) associated with the bead by the imaging processor.

b. Barcode Decoding by Image Processing Method

In other aspects, an imaging processing method can be used to decode an encoded pattern or a combination of encoded patterns (such as a barcode) associated with a bead (such as any of the beads disclosed herein). In one embodiment, the encoded pattern can be decoded on a slide or in the bottom of a microplate by the imaging processor. When beads are settled down and distributed on the bottom of a planar surface in a microplate, multiple beads can be decoded simultaneously with a wide viewing or scanning image camera. Microplates are standard and commonly used for high throughput assays. Both bar-code image and fluorescence image can be constructed on a conventional microscope or an inverted fluorescence microscope. Therefore, an experiment can be performed in the microplate without taking the beads out.

In one aspect, the imaging processor for decoding encoded patterns associated with any of the bead (such as, polymeric bead) compositions described herein has a light source for bead pattern illumination and an optical charge-coupled device (CCD) for capturing bead images in the bottom of the microwell. The CCD can be used for both barcode image and fluorescence detection. The CCD should have sufficient pixels to resolve the barcode pattern on beads. Optical filters can be used to select the excitation wavelength and fluorescence wavelength. In one embodiment, two light sources are used, one for barcode illumination in transmission mode and one for fluorescence excitation in reflection mode. Barcode illumination light source can be a white light, while fluorescence excitation light source can be a wavelength that matches the absorption of the fluorophore. By measuring the fluorescence intensity, beads having a positive biochemical reaction with the capture agent immobilized on the surface of the bead can be identified. By decoding the digital barcode image identifier, the identity of the capture agent immobilized on the surface of that bead can be identified.

In a further embodiment, the imaging processor can also comprise a reaction detection system (e.g., a fluorescence detector, an absorption detector, or a chemiluminescence detector) for detecting the result of reactions that have taken place between an analyte in a sample and the capture agent immobilized to the surface of the bead. In some embodiments, a signal-emitting entity can be used for detection of a positive or negative reaction between an analyte and the capture agent and the signal emitted from the signal emitting entity detected by the reaction detection system. The signal-emitting entity can be, without limitation, a fluorescence label, chemiluminescence label or other light-emitting label, an absorption label, or a radioactive label. Thus, for example, in configurations employing fluorescent signal-emitting entities, the reaction detection system can include a light source that produces light at an appropriate wavelength for activating the fluorescent material, as well as optics for directing the light source through an optically clear detection window for observing material in the sample cell. The light source can be any number of light sources that provide one or more appropriate wavelengths, including, e.g., lasers, laser diodes, and LEDs. Other light sources can be used in other detection systems. For example, broad band light sources can be employed in light scattering/transmissivity detection schemes, and the like.

In some aspects, the image of the encoded pattern identifier associated with a particular bead is analyzed using a script written for an image decoding program (such as, but not limited to, Matlab) to decode the encoded patterns based on imaging patterns from the beads. In some embodiments, the image decoding program can consist of four processes (1) enhancement of image; (2) segmentation of beads; (3) extraction of barcode slits; and (4) decoding of barcodes.

(i) Enhancement of Image

The process of decoding the encoded pattern (such as barcodes) identifiers associated with the bead compositions disclosed herein depends in part upon the quality of the image. The accuracy of the decoding process can be improved by imaging enhancement. This image enhancement can be performed via the use of image intensity normalization to provide uniform intensity background. Non-uniform background is often due to nonhomogeneous illumination. To achieve high image contrast of the beads, the homogeneous background should be produced first by background noise subtraction followed by normalization.

(ii) Segmentation of Beads

The goal of image segmentation is to outline the individual beads (such as, polymeric beads) in the image for further analysis. Basic segmentation routines track boundaries such as lines, curves in images that can locate the beads in the image. Since the beads of the compositions disclosed herein have constant area, each bead can be separated from the image after filtering using the beads' areas. In addition, the beads can be recognized based on the slits (bars) associated with the beads. The outline of the slits (bars) can be extracted using structure element transformation and filtration. With the good clarity of the slits, any noise in the background of the image can be removed.

(iii) Extraction of Barcode Slits

After segmentation of the beads, each bead can be processed separately in order to extract the barcodes. The areas of beads (such as, polymeric beads), extracted from the main image, are considered as subimages and are processed individually. The subimages show the orientation of the beads in random direction with the major and minor axis of the beads. The angles made by the major axis of the beads with the x-axis of the image can then be calculated. In one embodiment, extraction of slits from the beads is performed after rotating the beads to the x-axis. After the rotation of the beads, the borders of the beads are eliminated. The intensity values can be averaged along the length (y-axis) of the bars.

The intensity plot along the x-axis of the beads shows peaks with two widths (narrow and wide) corresponding to "1" and "0" bits.

(iv) Decoding of Bits

In order to decode the barcode, the widths of the transmission intensity peaks are analyzed. In one embodiment, a half maximum line is used to calculate the widths of the peaks. In order to extract the binary bit information, at least ten pixels (such as at least 1, 2, 3, 4, 5, 6, 7, 8, 9, or 10 pixels) are sufficient to describe the narrow slit ('0') of the encoded pattern associated with the beads (such as, polymeric beads). Depending on the rising or falling edges of the intensity peaks, the identity of the most significant bit (MSB) or least significant bit (LSB) of the encoded pattern (such as barcodes) can be identified. Subsequently, imaging software is used for image decoding 3. Bead Fluorescence Detection In a further aspect of the present invention, the identifier associated with any of the bead compositions described herein can be a fluorescent dye having a particular wavelength. The wavelength of the fluorescent dye associated with each bead can be decoded by an imaging processor to identify a capture agent that is bound to the surface of a particular bead in the plurality of beads.

In one embodiment, the imaging processor includes a fluorescence detector that measures fluorescence signal from a fluorescent dye associated with a bead that is an identifier for the capture agent immobilized to the surface of the bead. In another embodiment, the imaging processor further comprises a reaction detection system that measures fluorescence signal from a fluorescent dye associated with an analyte bound to the capture agent. In a further embodiment, the imaging processor includes a fluorescence detector that measures both fluorescence signal from a fluorescent dye associated with a bead that is an identifier for the capture agent immobilized to the surface of the bead and a reaction detection system for measuring a fluorescence signal from a fluorescent dye associated with an analyte bound to the capture agent, wherein the fluorescence signals comprise two separate and distinct wavelengths.

When a positive fluorescence signal is detected by the imaging processor, it indicates a positive reaction. In some embodiments, the reaction detector of the imaging processor comprises a light source, an optical filter, and a detector. The choice of light source depends on the fluorophore or fluorophores used in the assays and as identifiers for the capture agents immobilized to the surface of the beads. For example, red diode laser (665 nm), and compact Argon Laser (488 nm) or Helium laser, can be the light source for Picogreen and Cy 5.5 fluorophore. An optical filter can remove the reflected excitation light that is mixed in the fluorescence (e.g., Picogreen: 525 nm filter and Cy5.5: 694 nm filter). Cy 3 and Cy5 are commonly used fluorescence dyes; they can be excited with green light (530 nm) and red light (635 nm), respectively. The fluorescence intensity is commonly measured with a photomultiplier tube as the detector.

In another further embodiment, the imaging processor can also comprise a reaction detection system (e.g., a fluorescence detector, an absorption detector, or a chemiluminescence detector) for detecting the result of reactions that have taken place between an analyte in a sample and the capture agent immobilized to the surface of the bead (such as, a polymeric bead). In some embodiments, a signal-emitting entity can be used for detection of a positive or negative reaction between an analyte and the capture agent and the signal emitted from the signal emitting entity detected by the reaction detection system. The signal-emitting entity can be, without limitation, a fluorescence label, chemiluminescence label or other light-emitting label, an absorption label, or a radioactive label. Thus, for example, in configurations employing fluorescent signal-emitting entities, the reaction detection system can include a light source that produces light at an appropriate wavelength for activating the fluorescent material, as well as optics for directing the light source through an optically clear detection window for observing material in the sample cell. The light source can be any number of light sources that provide one or more appropriate wavelengths, including, e.g., lasers, laser diodes, and LEDs. Other light sources can be used in other detection systems. For example, broad band light sources can be employed in light scattering/transmissivity detection schemes, and the like.

In some aspects, the beads of any of the compositions described herein can be magnetic. In one embodiment, an electromagnet can be used to temporarily immobilize the bead for detection of fluorescent light.

4. RFID Chip Readers

In some aspects, the identifier associated with any of the bead compositions described herein can be a radio frequency. In some embodiments, an RFID chip reader component of an imaging processor can be used to emit an electromagnetic wave that causes a polymeric bead-embedded RFID chip to transmit a radio wave containing a unique identification code back to the RFID chip reader. Any commercially available RFID chip reader can be utilized in the methods described herein. Examples of RFID chip readers include, but are not limited to, those commercially available from FEC International (e.g., the AT-870, CS101, URP-SK110, CS461, FS-GF801, CS203ETHER Integrated RFID Reader, FS-GM251, and FS-GM252 RFID readers) and those commercially available from Hitachi, (e.g. the MRJ300, MRA200, MRE200, MRJ300, MRJ200, and MRJ010 RFID readers).

In another further embodiment, the imaging processor can also comprise a reaction detection system (e.g., a fluorescence detector, an absorption detector, or a chemiluminescence detector) for detecting the result of reactions that have taken place between an analyte in a sample and the capture agent immobilized to the surface of the bead. In some embodiments, a signal-emitting entity can be used for detection of a positive or negative reaction between an analyte and the capture agent and the signal emitted from the signal emitting entity detected by the reaction detection system. The signal-emitting entity can be, without limitation, a fluorescence label, chemiluminescence label or other light-emitting label, an absorption label, or a radioactive label. Thus, for example, in configurations employing fluorescent signal-emitting entities, the reaction detection system can include a light source that produces light at an appropriate wavelength for activating the fluorescent material, as well as optics for directing the light source through an optically clear detection window for observing material in the sample cell. The light source can be any number of light sources that provide one or more appropriate wavelengths, including, e.g., lasers, laser diodes, and LEDs. Other light sources can be used in other detection systems. For example, broad band light sources can be employed in light scattering/transmissivity detection schemes, and the like.

In some aspects, the beads (such as, polymeric beads) of any of the compositions described herein can be magnetic. In one embodiment, an electromagnet can be used to temporarily immobilize the bead for detection of radio frequency.

5. Machine Readable Formats for Supplying the Identity of Individual Beads

In some aspects of the methods provided herein, any of the unique identifiers associated with any of the beads disclosed herein can be identified by an imaging processor (such as any of the imaging processors described herein) and data corresponding to the identification stored on a fixed or data storage medium that is accessible via a system for reading the storage medium. In other aspects, the imaging processor further comprises a reaction detection system for detecting the binding of an analyte in a sample (such as a biological sample) by analyzing the binding of the analyte to the capture agent immobilized on the surface of the bead and data corresponding to the detected reaction stored on a fixed or data storage medium that is accessible via a system for reading the storage medium.

In some embodiments, for example, a system for reading a data storage medium can include a computer including a central processing unit ("CPU"), a working memory which can be, e.g., RAM (random access memory) or "core" memory, mass storage memory (such as one or more disk drives or CD-ROM drives), one or more display devices (e.g., cathode-ray tube ("CRT") displays, light emitting diode ("LED") displays, liquid crystal displays ("LCDs"), electroluminescent displays, vacuum fluorescent displays, field emission displays ("FEDs"), plasma displays, projection panels, etc.), one or more user input devices (e.g., keyboards, microphones, mice, touch screens, etc.), one or more input lines, and one or more output lines, all of which are interconnected by a conventional bidirectional system bus. The system can be a stand-alone computer, or can be networked (e.g., through local area networks, wide area networks, intranets, extranets, or the internet) to other systems (e.g., computers, hosts, servers, etc.). The system can also include additional computer controlled devices such as consumer electronics and appliances.

Input hardware can be coupled to the computer by input lines and can be implemented in a variety of ways. Machine-readable data of this invention can be inputted via the use of a modem or modems connected by a telephone line or dedicated data line. Alternatively or additionally, the input hardware can include CD-ROM drives or disk drives. In conjunction with a display terminal, a keyboard can also be used as an input device.

Output hardware can be coupled to the computer by output lines and can similarly be implemented by conventional devices. By way of example, the output hardware can include a display device for displaying a graphical representation of an active site of this invention using a program such as QUANTA. Output hardware might also include a printer, so that hard copy output can be produced, or a disk drive, to store system output for later use.

Machine-readable storage devices useful in the present invention include, but are not limited to, magnetic devices, electrical devices, optical devices, and combinations thereof. Examples of such data storage devices include, but are not limited to, hard disk devices, CD devices, digital video disk devices, floppy disk devices, removable hard disk devices, magneto-optic disk devices, magnetic tape devices, flash memory devices, bubble memory devices, holographic storage devices, and any other mass storage peripheral device. It should be understood that these storage devices include necessary hardware (e.g., drives, controllers, power supplies, etc.) as well as any necessary media (e.g., disks, flash cards, etc.) to enable the storage of data.

A person having skill in the art will appreciate that any other method or technique to communicate or store data is also contemplated for providing the unique identification code transmitted by an RFID chip from an individual polymeric bead in a machine readable format.

C. Methods for Conducting Multiplex Assays

Provided herein are methods for conducting multiplex biological or chemical assays using the bead (such as, polymeric bead) compositions described herein. Beads can be functionalized and bound with unique capture agents that specifically bind to one or more analytes (such as, but not limited to, chemical compounds or biomolecules in a sample (such as a biological sample)). Multiple capture agents can be functionalized to multiple beads within a single composition. However, each capture agent will be identifiable by an imaging processor based on the identifier associated with each individual bead.

In some aspects, a plurality of capture agent-bound beads can be added to a sample which contains one or more analytes followed by identification of one or more capture agents by an imaging processor based on the identity of the identifier associated with an individual bead. These beads and/or additional beads in the composition used for the multiplex assay can further be labeled with identifiers for purposes of specific information storage including, but not limited to, identification of the manufacturing lot number for the beads, identification of the assay for which the beads will be used, identification of a location, and/or identification of an individual. These beads and/or further beads in the composition can be labeled with identifiers for purposes of calibrating the imaging processor and or reaction detection system associated with the imaging processor.

In some aspects, information corresponding to any of the identifiers associated with individual beads in a plurality of beads (such as any of the beads of any of the bead compositions described herein) can be programmed to a memory, such as a computer. As used herein, a "memory" is a data storage unit (or medium) with programmable memory, preferably a non-volatile memory. As used herein, "programming" refers to the process by which data or information corresponding to a particular identifier is entered and stored in a memory. A memory that is programmed is a memory that contains retrievable information. It includes any means needed or used for writing to and reading from the memory. A "computer" is an instrument that has been programmed with or includes information (i.e., a key) specifying a code used to encode the identifiers. This instrument, or one linked thereto, transmits the programmed information and signals to the imaging processor and it receives information transmitted from the imaging processor upon receipt of the appropriate signal. The computer thus creates the appropriate signal to transmit to the imaging processor and can also interpret transmitted signals. For example, if a "1" is stored at position 1,1 in the memory of the computer, upon receipt of this corresponding information from the imaging processor, the computer can determine that this means the identifier corresponding to a capture agent is, for example, a peptide containing alanine at the N-terminus, an organic group, organic molecule, oligonucleotide or whatever this information has been predetermined to mean. In another embodiment, upon receipt of this corresponding information from the imaging processor, the computer can determine that this means the identifier corresponds to the identity of a manufacturing lot, a locational identifier, or an individual, or whatever this information has been predetermined to mean. Alternatively, the information sent to and transmitted from the computer can be encoded into the appropriate form by an individual. In some embodiments, the computer is a remote computer that is accessible by a remote accessibility means, for example, the internet. In other embodiment, the computer is programmed information (i.e., a key) specifying a code used to encode the identifiers via software provided by an external source (such as, but not limited to, a compact disk, a CD-ROM, or a downloadable program obtained over the internet).

In other aspects, the imaging processor comprises a reaction detection system for detecting the binding of an analyte in a sample (such as a biological sample). In some embodiments, the reaction detection system analyzes the binding of the analyte to the capture agent immobilized on the surface of a bead in a plurality of beads and data corresponding to the detected reaction is transmitted to a computer. The detection system can be operably coupled to a computer, e.g., via an analog to digital converter, for transmitting detected signal data to the computer for analysis, storage, data manipulation, or integration with other information obtained from the identification of identifiers by the imaging processor. The computer can integrate and store information related to the identity of the identifier associated with the capture agent with information related to the binding of an analyte to the capture agent that is detected by the reaction detection system. In another embodiment, the computer integrates and stores information related to the identity of the identifier associated with the capture agent with information related to the binding of an analyte to the capture agent that is detected by the reaction detection system along with information obtained from one or more bead present within the plurality of beads (such as, polymeric beads) with an identifier that is recognized by the imaging processor as corresponding to, without limitation, a manufacturing lot, a locational identifier, and/or an individual.

In another embodiment of the present invention, the analysis is multiplexed, that is, each sample is analyzed so that a signal from the signal emitting entity is detected by the reaction detection system for at least 2 analytes of interest, at least 3 analytes of interest, at least 4 analytes of interest, at least 5 analytes of interest, at least 10 analytes of interest, at least 15 analytes of interest, at least 20 analytes of interest, at least 25 analytes of interest, at least 30 analytes of interest, at least 35 analytes of interest, at least 40 analytes of interest, at least 45 analytes of interest, or at least 50 analytes of interest, or more. In one embodiment, the data are then subjected to an iterative minimization of error algorithm that takes into account variance between the datasets obtained from replicates, for example using least squares, least absolute error, etc.; and/or a monotone transformation algorithm that stabilizes the variability of the data and considers background measurements. An exemplary method for use of the compositions of beads (such as, polymeric beads) encoded with unique identifiers described herein is illustrated in FIG. 1.

Accordingly, provided herein is a method for conducting a multiplex assay comprising the steps of: contacting a sample with beads (such as, polymeric beads) in an assay system, wherein each bead in the system comprises an identifier; wherein the system comprises (i) at least one bead (such as, a polymeric bead) with an identifier that is recognized by an imaging processor as a specific assay, and (ii) a plurality of beads (such as, polymeric beads), wherein each bead comprises a capture agent immobilized on the surface of the bead that specifically binds to an analyte; and simultaneously or sequentially, in any order: identifying the identifier that is recognized by the imaging processor as the specific assay; and detecting the binding of the analyte in the sample by analyzing the binding of the analyte to the capture agent immobilized on the surface of the bead (such as, a polymeric bead) based on the identification of the identifier as the specific assay. In one embodiment, the system further comprises at least one bead (such as, a polymeric bead) with an identifier that is recognized by the imaging processor as corresponding to a manufacturing lot. In another embodiment, the identifier that is recognized by the imaging processor as corresponding to a manufacturing lot is additionally recognized by the imaging processor as identifying the bead as a positive or negative control. In another embodiment, the system further comprises at least one bead (such as, a polymeric bead) with an identifier that is recognized by the imaging processor as corresponding to an individual. In a further embodiment, the system further comprises at least one bead (such as, a polymeric bead) with an identifier that is recognized by the imaging processor as corresponding to a location. The locational identifier can correspond to such locations as, but not limited to, a hospital, a diagnostic laboratory, an address, a health care professional's office, or a research laboratory. In yet another embodiment, the system further comprises at least one bead (such as, a polymeric bead) that is pre-labeled for calibration of the imaging processor. In other embodiments, the system further comprises at least one bead (such as, a polymeric bead) that is pre-labeled for monitoring functions of the imaging processor. In some embodiments, the identifier is an encoded pattern or a combination of encoded patterns, a radio frequency (such as an RFID signal), or a fluorescent signal (such as a gradient). In another embodiment, the imaging processor further comprises a reaction detection system for detecting the binding of the analyte in the sample by analyzing the binding of the analyte to the capture agent.

In some embodiments, the beads (such as, polymeric beads) comprise a spherical or rectangular shape. In another embodiment, the beads (such as, polymeric beads) are less than about 300 µm in diameter. In still other embodiments, the surface of the bead (such as, a polymeric bead) is smooth and lacks surface irregularities. In some embodiments, the surface of the bead (such as, a polymeric bead) comprises at least one site for chemical attachment of the capture agent. In a further embodiment, the beads (such as, polymeric beads) are magnetic.

In some embodiments, the sample contains one or more analytes capable of binding to the capture agent. Such biomolecules include, but are not limited to, a DNA molecule, a DNA-analog-molecule, an RNA-molecule, an RNA-analog-molecule, an amino-acid, a nucleotide, a protein, an enzyme, a lipid, a phospholipid, a carbohydrate moiety, a polysaccharide, an antigen, a virus, a cell, an antibody, a small molecule chemical compound, or an antibody fragment. In other embodiments, the sample contains chemical compounds capable of binding to the capture agent. Any chemical compound capable of binding to the capture agent can be present in the sample including, but not limited to, individual components of chemical libraries, small molecules, or environmental toxins (for example, pesticides or heavy metals).

In some aspects, the analytes in a sample (such as a biological sample) can be labeled with a signal-emitting entity capable of emitting a detectable signal upon binding to the capture agent. In some embodiments, the signal-emitting entity can be colorimetric based. In other embodiments, the signal-emitting entity can be fluorescence-based including, but not limited to, phycoerythrin, blue fluorescent protein, green fluorescent protein, yellow fluorescent protein, cyan fluorescent protein, and derivatives thereof. In other embodiments, the signal-emitting entity can be radio-isotope based, including, but not limited to, molecules labeled with $^{32}P$, $^{33}P$, $^{22}Na$, $^{36}Cl$, $^{2}H$, $^{3}H$, $^{35}S$, and $^{123}I$. In other embodiments, the signal-emitting entity is light-based including, but not limited to, luciferase (e.g. chemiluminescence-based), horseradish peroxidase, alkaline phosphatase and derivatives thereof. In some embodiments, the biomolecules or chemical compounds present in the sample can be labeled with the signal-emitting entity prior to contact with the bead composition. In other embodiments, the biomolecules or chemical compounds present in the sample can be labeled with the signal-emitting entity subsequent to contact with the bead composition.

V. Kits

In further aspects, provided herein are kits for conducting multiplex assays. In some embodiments, the kits comprise at least one bead (such as, a polymeric bead) with an identifier that is recognized by an imaging processor as a specific assay; and one or more of a) a plurality of beads (such as, polymeric beads), wherein each bead comprises i) an identifier, and ii) a capture agent immobilized on the surface of the bead that specifically binds to an analyte, wherein the identifier corresponds to the capture agent; b) a signal-emitting entity capable of directly or indirectly binding to the analyte or capture agent; c) at least one bead (such as, a polymeric bead) with an identifier that is recognized by the imaging processor as corresponding to a manufacturing lot; d) at least one bead (such as, a polymeric bead) with an identifier that is recognized by the imaging processor as corresponding to an individual; e) at least one bead (such as, polymeric bead) with an identifier that is recognized by the imaging processor as corresponding to a locational identifier; or f) at least one bead (such as, a polymeric bead) that is pre-labeled for calibration of the imaging processor.

In some embodiments, the beads comprise a spherical or rectangular shape. In another embodiment, the beads are less than about 300 µm in diameter. In still other embodiments, the surface of the bead is smooth and lacks surface irregularities. In some embodiments, the surface of the bead comprises at least one site for chemical attachment of the capture agent. In a further embodiment, the beads are magnetic.

The kits of the present invention can be used to detect analytes in a sample (such as a biological sample). Analytes can include, but are not limited to, a DNA molecule, a DNA-analog-molecule, an RNA-molecule, an RNA-analog-molecule, an amino-acid, a nucleotide, a protein, an enzyme, a lipid, a phospholipid, a carbohydrate moiety, a polysaccharide, an antigen, a virus, a cell, an antibody, a small molecule chemical compound, or an antibody fragment. In other embodiments, the analyte is a chemical compound (such as a small molecule chemical compound) capable of binding to the capture agent such as individual components of chemical libraries, small molecules, or environmental toxins (for example, pesticides or heavy metals).

In some aspects, the analytes in a sample (such as a biological sample) can be labeled with a signal-emitting entity capable of emitting a detectable signal upon binding to the capture agent. In some embodiments, the signal-emitting entity can be colorimetric based. In other embodiments, the signal-emitting entity can be fluorescence-based including, but not limited to, phycoerythrin, blue fluorescent protein, green fluorescent protein, yellow fluorescent protein, cyan fluorescent protein, and derivatives thereof. In other embodiments, the signal-emitting entity can be radio-isotope based, including, but not limited to, molecules labeled with $^{32}P$, $^{33}P$, $^{22}Na$, $^{36}Cl$, $^{2}H$, $^{3}H$, $^{35}S$, and $^{123}I$. In other embodiments, the signal-emitting entity is light-based including, but not limited to, luciferase (e.g. chemiluminescence-based), horseradish peroxidase, alkaline phosphatase, and derivatives thereof. In some embodiments, the biomolecules or chemical compounds present in the sample can be labeled with the signal-emitting entity prior to contact with the bead composition. In other embodiments, the biomolecules or chemical compounds present in the sample can be labeled with the signal-emitting entity subsequent to contact with the bead composition.

In other aspects, the kits of the present invention can further comprise an imaging processor. In one embodiment, the imagining processor can be used for identifying the at least one bead (such as, a polymeric bead) with an identifier that is recognized by the imaging processor as a specific assay. In another embodiment, the imagining processor can be used for identifying the identifier on the plurality of beads (such as, polymeric beads), wherein the identifier corresponds to the identity of the capture agent immobilized on the surface of the beads. In further embodiments, the imaging processor further comprises a reaction detection system that can be used to detect the amount of signal produced by the signal-emitting entity capable of directly or indirectly binding to the analyte or capture agent. In another embodiment, the imaging processor can be used for identifying the identifier on the at least one bead (such as, a polymeric bead) with an identifier that is recognized by the imaging processor as a manufacturing lot. In another embodiment, the imaging processor can be used for identifying the identifier on the at least one bead (such as, a polymeric bead) with an identifier that is recognized by the imaging processor as an individual. In another embodiment, the imagining processor can be used for identifying the identifier on the at least one bead (such as, a polymeric bead) with an identifier that is recognized by the imaging processor as corresponding to a locational identifier. In another embodiment, the imaging processor can be used for identifying the identifier on the at least one bead (such as, a polymeric bead) that is pre-labeled for calibration of the imaging processor. In a further embodiment, the imaging processor has an RFID chip reader as a component. In another embodiment, the imaging processor has a reaction detection system as a component.

In another aspect, the kits of the present invention can further comprise an entity capable of directly or indirectly binding to the analyte or capture agent, wherein the entity comprises an affinity tag. The affinity tag can be any affinity tag known and used in the art, such as, but not limited to, biotin, polyhistidine (such as $His_6$), or maltose binding protein.

In still other aspects, the kits of the present invention can further comprise at least one bead that is pre-labeled for monitoring functions of the imaging processor.

VI. Systems

In other aspects, provided herein are multiplex assay systems. In some embodiments, the systems comprise a plurality of beads (such as, polymeric beads), such as any of the beads disclosed in any of the compositions, methods, or kits provided herein. The system also comprises an apparatus comprising an imaging processor system and a reaction detection system, wherein the identification of an identifier that corresponds to one or more of a specific assay, a specific capture agent, a manufacturing lot, an individual, a locational identifier, and/or a calibration signal by the imaging processor in the decoding system activates the use of a software analyzing detection signals detected by the reaction detection system correlated to the specific assay.

Example

This example describes an exemplary assay kit for a multiplex biological assay using compositions of beads encoded with unique information-storing identifiers.

Materials and Methods

Bead Compositions

A plurality of beads were functionalized and bound with two different capture agents: antibodies against each of tumor necrosis factor-alpha (TNF-α) and interleukin 6 (IL-6). The beads bound with antibodies against TNF-α were labeled with barcode 1011. The beads bound with antibodies against IL-6 were labeled with barcode 1012.

An additional plurality of beads were coated with biotinylated bovine serum albumin (BSA) and served as the positive control. These beads comprised a barcode 3023 corresponding to the coating of biotinylated BSA, as well as to the identity of the assay kit ("Demo Kit").

An additional plurality of beads were coated with BSA and served as the negative control. These beads comprised barcode 3024 or 3025 corresponding to the coating of BSA, as well as to the lot number PB031313-1 of the assay kit and the corresponding calibration data specific to the lot number.

An additional bead coated with BSA was labeled with a barcode 4013 corresponding to a particular patient ID 116707189.

An additional bead coated with BSA was labeled with a barcode 3080 corresponding to the research laboratory in which the assay was performed (PlexBio).

Reaction with Sample

The pluralities of beads described above were added to a well (A2) containing a sample of serum spiked with TNF-α and IL-6. The mixture was then incubated at 37° C. for one hour. The sample was then washed with wash buffer (phosphate buffered saline containing 0.1% polysorbate 20 (Tween 20)). A biotin/secondary antibody solution was then added to the sample, containing biotinylated secondary antibodies capable of binding to TNF-α or IL-6 already bound with their primary antibodies. The sample was then incubated and washed with wash buffer. A solution containing streptavidin-phycoerythrin (PE) conjugate was then added and incubated with the bead mixture. The solution was then washed with wash buffer and a signal stabilizing solution to remove the excess fluorescent molecules.

Simultaneously, the pluralities of beads described above were added to eight other wells (A1, B1, C1, D1, E1, F1, G1, H1) containing known but different concentrations of TNF-α and IL-6, and the same assay process was carried out on these wells.

An imaging processor and reaction detection system were then used to simultaneously identify the barcode on each bead and detect the signal emitted from streptavidin-PE for all nine wells. A standard curve was determined for each of TNF-α and IL-6 using the identifications and signals detected from wells A1, B1, C1, D1, E1, F1, G1, H1, in combination with the known concentrations in each well. The median signal emitted by beads bound with the antibodies against TNF-α and IL-6 was then inputted into the standard curve for each of TNF-α and IL-6 to estimate the concentration of each in the sample.

Results

Figure 3A:
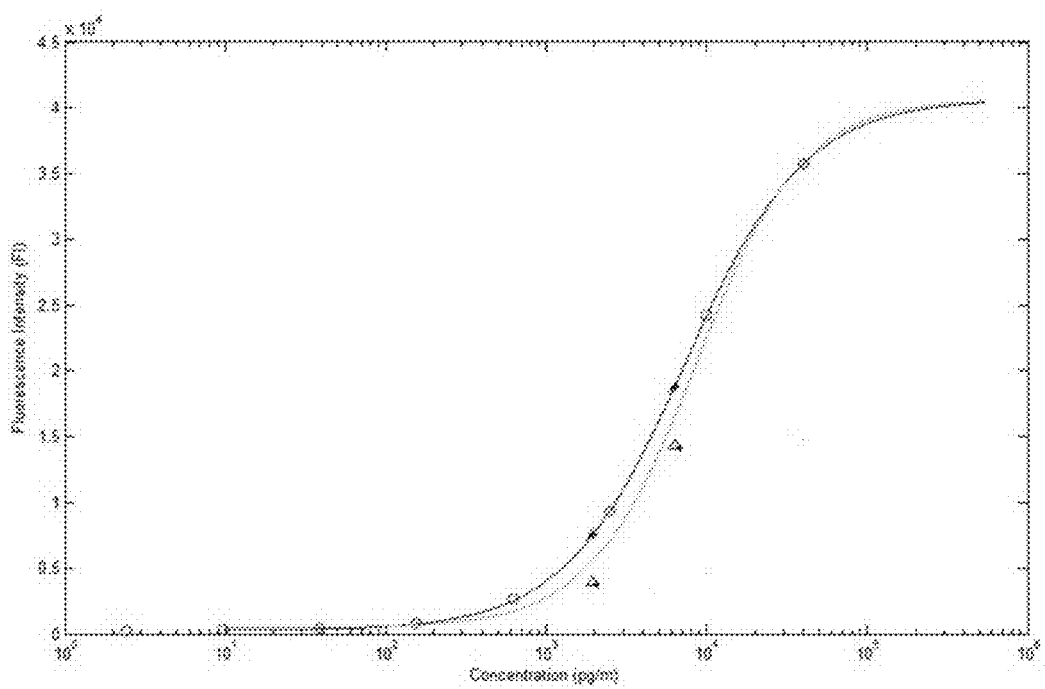
FIG. 3A-3B are a graphical representations of standard curves calculated for the exemplary multiplex biological assay of FIGS. 2A-2C.
Figure 3B:
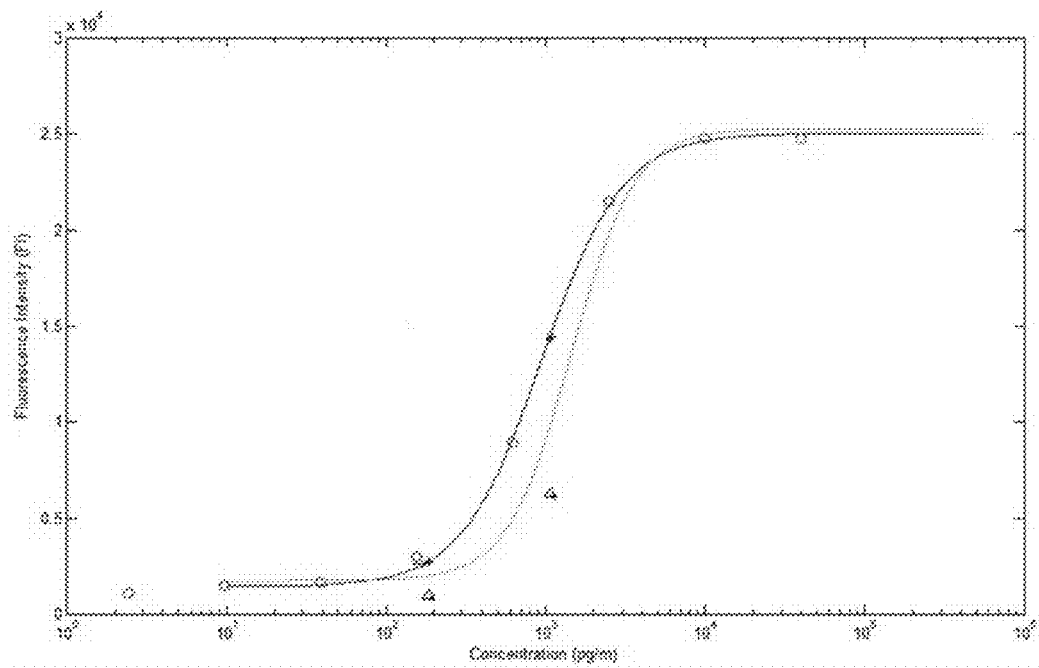

FIGS. 2A-2C show the results. FIG. 2A shows the identification of the assay kit ("Demo Kit"), the identification of the lot number ("PB031313-1"), the identification of the patient ID ("116707189"), and the testing lab ("PlexBio"). The identification of the assay kit as "Demo Kit" indicates that the analytes to be measured are TNF-α and IL-6. FIG. 2B shows the measurements from wells A1, B1, C1, D1, E1, F1, G1, H1 used to determine the standard curve. FIG. 3A is a graphical representation of the standard curve for TNF-α. FIG. 3B is a graphical representation of the standard curve for IL-6. For each well, the known concentration is shown, along with the median fluorescence intensity for beads 1011 bound with antibodies against TNF-α and beads 1012 bound with antibodies against IL-6. FIG. 2C shows the measurements from well A2. The median fluorescence intensity for the beads 1011 bound with antibodies against TNF-α was measured to be 14,421, and the median fluorescence intensity for the beads 1012 bound with antibodies against IL-6 was measured to be 2,770.

The example, which is intended to be purely exemplary of the invention and should therefore not be considered to limit the invention in any way, also describes and details aspects and embodiments of the invention discussed above. The foregoing examples and detailed description are offered by way of illustration and not by way of limitation. All publications, patent applications, and patents cited in this specification are herein incorporated by reference as if each individual publication, patent application, or patent were specifically and individually indicated to be incorporated by reference. In particular, all publications cited herein are expressly incorporated herein by reference for the purpose of describing and disclosing compositions and methodologies which might be used in connection with the invention. Although the foregoing invention has been described in some detail by way of illustration and example for purposes of clarity of understanding, it will be readily apparent to those of ordinary skill in the art in light of the teachings of this invention that certain changes and modifications can be made thereto without departing from the spirit or scope of the appended claims.

What is claimed is:

1. A method for conducting a multiplex assay comprising the steps of:
    1) contacting a sample with beads in an assay system, wherein the system comprises:
        (a) a plurality of beads comprising at least a first bead and a second bead,
            wherein the first bead comprises:
                (i) a first capture agent immobilized on the surface of the bead that specifically binds to a first analyte, and
                (ii) a first identifier that is recognized by an imaging processor as corresponding to the first capture agent; and
            wherein the second bead comprises:
                (iii) a second capture agent immobilized on the surface of the bead that specifically binds to a second analyte, and
                (iv) a second identifier that is recognized by an imaging processor as corresponding to the second capture agent, wherein the second identifier is different from the first identifier; and
        (b) at least a third bead, wherein the third bead comprises a third identifier that is recognized by an imaging processor as corresponding to a manufacturing lot, wherein the third identifier does not correspond to a capture agent associated with the third bead;
    wherein the first, second, and third identifiers are visually encoded patterns or combinations of visually encoded patterns; and
    simultaneously or sequentially, in any order:
    2) identifying the first identifier;
    3) identifying the second identifier;
    4) identifying the third identifier; and
    5) detecting the binding of the first and second analytes to the first and second capture agents.

2. The method of claim 1, wherein the first and the second analytes are different.

3. The method of claim 1, wherein the third identifier is different from the first and second identifiers.

4. The method of claim 1, wherein the system further comprises (c) at least a fourth bead that is pre-labeled for monitoring functions of the imaging processor.

5. The method of claim 1, wherein the first, second, and third beads comprise a spherical or rectangular shape.

6. The method of claim 1, wherein the first, second, and third beads are less than about 300 µm in diameter.

7. The method of claim 1, wherein the surfaces of the first, second, and third beads are smooth and lack surface irregularities.

8. The method of claim 1, wherein the surfaces of the first and the second beads both comprise at least one site for chemical attachment of the first or second capture agents.

9. The method of claim 1, wherein the first and second capture agents are each independently selected from the group consisting of: a DNA molecule, a DNA-analog-molecule, an RNA-molecule, an RNA-analog-molecule, a polynucleotide, a protein, an enzyme, a lipid, a phospholipid, a carbohydrate moiety, a polysaccharide, an antigen, a virus, a cell, an antibody, and an antibody fragment.

10. The method of claim 1, wherein one or more of the first, second, and third beads are magnetic.

11. A kit for conducting a multiplex assay comprising:
    (a) a plurality of beads comprising at least a first bead and a second bead,
        wherein the first bead comprises:
            (i) a first capture agent immobilized on the surface of the bead that specifically binds to a first analyte, and
            (ii) a first identifier that is recognized by an imaging processor as corresponding to the first capture agent; and
        wherein the second bead comprises:
            (iii) a second capture agent immobilized on the surface of the bead that specifically binds to a second analyte, and
            (iv) a second identifier that is recognized by an imaging processor as corresponding to the second capture agent, wherein the second identifier is different from the first identifier; and
    (b) at least a third bead, wherein the third bead comprises a third identifier that is recognized by an imaging processor as corresponding to a manufacturing lot, wherein the third identifier does not correspond to a capture agent associated with the third bead; and
    wherein the first, second, and third identifiers are visually encoded patterns or combinations of visually encoded patterns.

12. The kit of claim 11, wherein the first and second analytes are different.

13. The kit of claim 11, wherein the third identifier is different from the first and second identifiers.

14. The kit of claim 11, wherein the kit further comprises (c) a signal-emitting entity capable of directly or indirectly binding to the first analyte or the first capture agent, and directly or indirectly binding to the second analyte or the second capture agent.

15. The kit of claim 14, wherein the signal-emitting entity indirectly binds to the first analyte or the first capture agent, and the second analyte or the second capture agent, via a secondary antibody that is conjugated to the signal-emitting entity.

16. The kit of claim 14, wherein the signal-emitting entity indirectly binds to the first analyte or the first capture agent, and the second analyte or the second capture agent, via a nucleotide probe that is conjugated to the signal-emitting entity.

17. The kit of claim 14, wherein the signal-emitting entity is phycoerythrin, GFP, RFP, CFP, YFP, FITC, horseradish peroxidase, alkaline phosphatase, or a radiolabel.

18. The kit of claim 14, wherein the kit further comprises (d) an imaging processor for
   (v) identifying the first identifier;
   (vi) identifying the second identifier;
   (vii) identifying the third identifier; and
   (viii) detecting the amount of signal produced by the signal-emitting entity of (c).

19. The kit of claim 18, further comprising (e) an entity capable of directly or indirectly binding to the first analyte or the first capture agent and directly or indirectly binding to the second analyte or the second capture agent, wherein the entity comprises an affinity tag.

20. The kit of claim 19, wherein the affinity tag is biotin, $His_6$, or maltose.

21. The kit of claim 19, further comprising (f) at least a fourth bead that is pre-labeled for monitoring functions of the imaging processor.

22. The kit of claim 11, wherein the first, second, and third beads comprise a spherical or rectangular shape.

23. The kit of claim 11, wherein the first, second, and third beads are less than about 300 µm in diameter.

24. The kit of claim 11, wherein the surfaces of the first, second, and third beads are smooth and lack surface irregularities.

25. The kit of claim 11, wherein the surfaces of the first and the second beads both comprise at least one site for chemical attachment of the first or second capture agent.

26. The kit of claim 11, wherein the first and second capture agents are each independently selected from the group consisting of: a DNA molecule, a DNA-analog-molecule, an RNA-molecule, an RNA-analog-molecule, a polynucleotide, a protein, an enzyme, a lipid, a phospholipid, a carbohydrate moiety, a polysaccharide, an antigen, a virus, a cell, an antibody, a small molecule, and an antibody fragment.

27. The kit of claim 11, wherein one or more of the first, second, and third beads are magnetic.

28. A multiplex assay system comprising:
   1) the first, second, and third beads of the kit of claim 11;
   2) an apparatus comprising an imaging processor system and a reaction detection system; and
   3) software configured to identify the first, second, or third identifiers as imaged by the imaging processor system and analyze signals as detected by the reaction detection system.

29. The method of claim 1, wherein the plurality of beads comprises more than 20 beads.

30. The method of claim 1, wherein the plurality of beads comprises more than 100 beads.

31. The kit of claim 11, wherein the plurality of beads comprises more than 20 beads.

32. The kit of claim 11, wherein the plurality of beads comprises more than 100 beads.

* * * * *